(12) United States Patent
Ziv et al.

(10) Patent No.: US 9,192,680 B2
(45) Date of Patent: *Nov. 24, 2015

(54) PHARMACEUTICAL COMPOUNDS

(71) Applicant: APOSENSE LTD., Petach-Tikva (IL)

(72) Inventors: Ilan Ziv, Kfar Saba (IL); Hagit Grimberg, Herzliya (IL)

(73) Assignee: Aposense LTD., Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/540,281

(22) Filed: Nov. 13, 2014

(65) Prior Publication Data

US 2015/0072949 A1    Mar. 12, 2015

Related U.S. Application Data

(60) Continuation-in-part of application No. 13/961,905, filed on Aug. 8, 2013, now Pat. No. 8,916,537, which is a division of application No. 12/791,364, filed on Jun. 1, 2010, now Pat. No. 8,530,444.

(51) Int. Cl.

| *A61K 47/48* | (2006.01) |
| *A61K 31/7068* | (2006.01) |
| *A61K 31/513* | (2006.01) |
| *A61K 31/4745* | (2006.01) |
| *C07D 403/04* | (2006.01) |
| *C07D 239/10* | (2006.01) |
| *C07H 19/06* | (2006.01) |
| *C07D 491/22* | (2006.01) |

(52) U.S. Cl.
CPC ....... *A61K 47/48061* (2013.01); *A61K 31/4745* (2013.01); *A61K 31/513* (2013.01); *A61K 31/7068* (2013.01); *A61K 47/48023* (2013.01); *C07D 239/10* (2013.01); *C07D 403/04* (2013.01); *C07D 491/22* (2013.01); *C07H 19/06* (2013.01)

(58) Field of Classification Search
CPC ... C07D 403/04; C07D 239/10; C07D 491/22
USPC .......................................... 514/49, 274, 283
See application file for complete search history.

(56) References Cited

U.S. PATENT DOCUMENTS

| 5,464,826 | A |  | 11/1995 | Grindey et al. |
| 6,090,800 | A | * | 7/2000 | Unger et al. ................. 514/180 |
| 7,270,799 | B2 |  | 9/2007 | Ziv et al. |
| 7,638,528 | B2 | * | 12/2009 | Kucera et al. ................. 514/283 |
| 2003/0186924 | A1 |  | 10/2003 | Zhou et al. |
| 2006/0264397 | A1 |  | 11/2006 | Kucera et al. |

FOREIGN PATENT DOCUMENTS

| JP | S57154190 | 9/1982 |
| JP | 6019790 | 1/1985 |
| JP | S61-85389 | 4/1986 |
| JP | 2003-313186 | 11/2003 |
| JP | 2007-513901 | 5/2007 |
| WO | WO 2008/081447 | 7/2008 |
| WO | WO 2010/150255 | 12/2010 |

OTHER PUBLICATIONS

Gura, "Cancer models: systems for identifying new drugs are often faulty", Science, Nov. 1997, vol. 278, No. 5340 pp. 1041-1042.
The Merck Manual, 16th adtion, 1992, pp. 1263, 1266-1269, 1274 and 1292.
European Search Report mailed on Oct. 22, 2013 for European Application No. 11789347.9.
Office Action mailed on Jan. 3, 2014 for U.S. Appl. No. 13/961,905.
Office Action mailed on May 16, 2014 for U.S. Appl. No. 13/961,905.
Notice of Allowance mailed on Sep. 2, 2014 for U.S. Appl. No. 13/961,905.
International Search Report mailed on Nov. 2, 2011, for International Application No. PCT/IL2011/000425.
Office Action mailed on Jun. 21, 2012 for U.S. Appl. No. 12/791,364.
Notice of Allowance mailed on May 10, 2013 for U.S. Appl. No. 12/791,364.

* cited by examiner

*Primary Examiner* — Ganapathy Krishnan
(74) *Attorney, Agent, or Firm* — Pearl Cohen Zedek Latzer Baratz LLP

(57) ABSTRACT

Novel compounds and pharmaceutical compositions are provided. In one aspect of the invention the compounds may be utilized in medical practice for treating pancreatic cancer.

11 Claims, 19 Drawing Sheets

* Not detected

PHARMACEUTICAL COMPOUNDS

CROSS-REFERENCE TO RELATED APPLICATIONS

This application is a continuation in part of U.S. patent application Ser. No. 13/961,905, filed Aug. 8, 2013, which is a Divisional of U.S. patent application Ser. No. 12/791,364, now U.S. Pat. No. 8,530,444 filed Jun. 1, 2010, which are both hereby incorporated by reference.

FIELD OF THE INVENTION

The invention relates to the field of drug therapy for cancer. Specifically, the invention relates to novel compounds and pharmaceutical compositions that may be utilized for the treatment of pancreatic cancer.

BACKGROUND OF THE INVENTION

Drug therapy for medical disorders often requires improvement in aspects such as pharmacokinetics, efficacy, or adverse effects. For example, many anti-cancer drugs have a very narrow therapeutic window, i.e., a small difference between the drug levels required to exert a beneficial anti-tumor effect, and those causing adverse effects, some of which may be dose-limiting or life-risking. As another example, it is often desirable for many drugs used in various fields, such as anti-cancer drugs, anti-inflammatory drugs, or drugs used to treat neurological or psychiatric disorders, to be administered as inactive pro-drugs, with a subsequent slow, sustained release of the active drug, thereby enabling prolonged drug circulation time and prolonged drug activity at its target sites. Furthermore, it is often desirable for a drug, to be targeted to a focus of disease, i.e., to have, following its administration to the patient, a concentration gradient between target and non-target tissues, with relatively high levels of the pro-drug and/or the active drug at the foci of disease, compared to non-target tissues.

SUMMARY OF THE INVENTION

In an embodiment of the invention, there is provided a method of treating pancreatic cancer in a subject in need comprising administering to the subject a therapeutically effective dose of compound represented by the structure set forth in Formula (II)

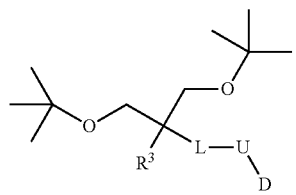

Formula (II)

in which
R$^3$ is selected from the group consisting of hydrogen, $C_1$, $C_2$, $C_3$, $C_4$, $C_5$, $C_6$, $C_7$ and $C_8$ linear or branched alkyl;
L is selected from the group consisting of $C_1$, $C_2$, $C_3$, $C_4$, $C_5$, $C_6$, $C_7$ or $C_8$ linear, branched or cyclic alkyl, $C_1$, $C_2$, $C_3$, $C_4$, $C_5$, $C_6$, $C_7$ or $C_8$ linear, branched alkyl-amine, piperidinyl, aryl, or a combination thereof;
U is selected from the group consisting of —O—; —(CO) O—; —O(CO)—NH—; and —(CO)—NH—
D is an anti-cancer drug; and
pharmaceutically acceptable salts, hydrates, solvates and metal chelates of the compound.

In some embodiments, R$^3$ in the compound of formula II is a methyl.

In some embodiments of the invention, there is provided a method of treating pancreatic cancer in a subject in need comprising administering to the subject in need a compound according to the structure set forth in Formula (III)

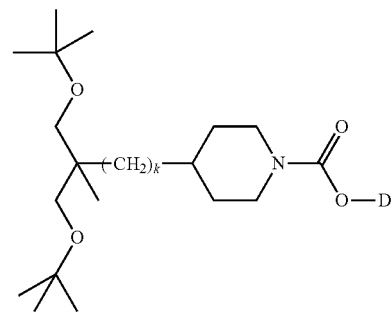

Formula (III)

wherein k is an integer selected from the group consisting of 1,2,3,4 and 5;
and pharmaceutically acceptable salts, hydrates, solvates and metal chelates of the compound.

In some embodiments of the invention, there is provided a method of treating pancreatic cancer in a subject in need comprising administering to the subject in need a compound according to the structure set forth in Formula (IV)

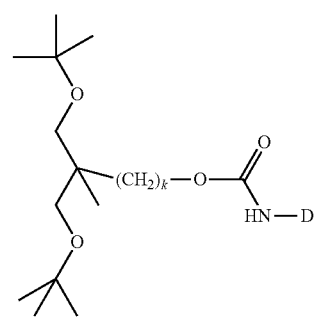

Formula (IV)

wherein k is an integer selected from the group consisting of 1,2 or 3; and pharmaceutically acceptable salts, hydrates, solvates and metal chelates of the compound.

In some embodiments of the invention, there is provided a method of treating pancreatic cancer in a subject in need comprising administering to the subject in need a compound according to the structure set forth in Formula (VI)

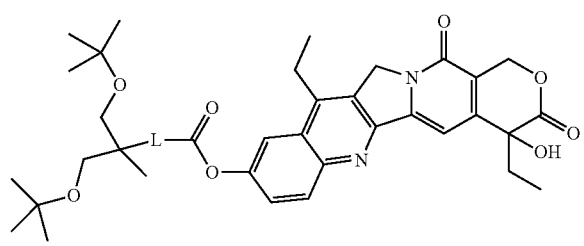

Formula (VI)

and pharmaceutically acceptable salts, hydrates, solvates and metal chelates of the compound.

In some embodiments of the invention, there is provided a method of treating pancreatic cancer in a subject in need comprising administering to the subject in need a compound according to the structure set forth in Formula (VII)

Formula (VII)

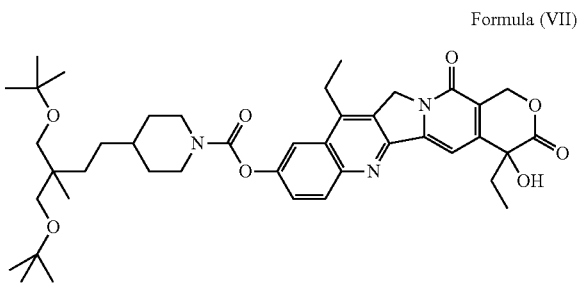 [SMILES: CCc1c2c(nc3ccc(OC(=O)N4CCC(CCC(C)(COC(C)(C)C)COC(C)(C)C)CC4)cc13)-c1cc3c(c(=O)n1C2)COC(=O)C3(O)CC]

In some embodiments of the invention, there is provided a method of treating pancreatic cancer in a subject in need comprising administering to the subject in need a compound according to the structure set forth in Formula (VIII)

Formula (VIII)

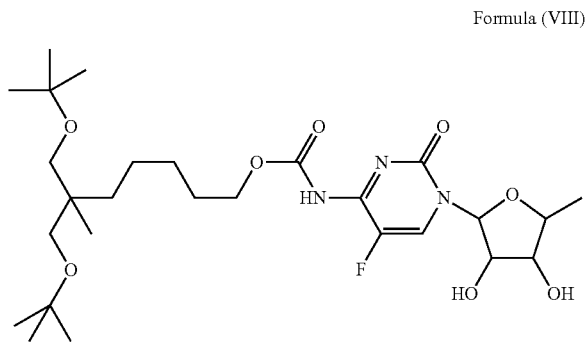 [SMILES: CC1OC(n2cc(F)c(NC(=O)OCCCCCC(C)(COC(C)(C)C)COC(C)(C)C)nc2=O)C(O)C1O]

In some embodiments of the invention, D is a topoisomerase inhibitor

In some embodiments of the invention, D is a camptothecin

In some embodiments of the invention, D is 5-fluorouracil.

The method according to claim 10 wherein D is capecitabine.

The term "drug" for the purpose of the present invention relates to a medicinally-useful chemical compound, which upon administration to a subject with a disease, exerts a pharmacological effect, such as helping to cure the disease, reducing its extent, or alleviating its symptoms or signs.

The term "conjugate" for the purpose of the present invention, relates to a molecule that comprises two (or more) chemical moieties, linked together by any means known in the art.

The term "therapeutically effective dose" relates, for example, to an amount of drug that elicits a therapeutically useful response, either in treatment of an existing medical disorder, and/or in preventing or delaying the disease onset, in an animal or a human subject.

BRIEF DESCRIPTION OF THE FIGURES

The invention will now be described in relation to certain examples and preferred embodiments, with reference to the following illustrative figures. In the Figures:

FIG. 6A shows plasma concentrations of the parent drugs ATT-11T or CPT-11 vs. time, while FIG. 6B shows the plasma concentrations of the common active cytotoxic metabolite SN-38 vs. time. As shown, ATT-11T was characterized by favorable profile, with sustained plasma levels and slow clearance of both the parent drug and its active metabolite SN-38, as compared to CPT-11.

Therefore, administration of ATT-11T resulted in a substantially longer exposure to both the parent drug and to its active metabolite SN-38, as compared to CPT-11.

Figure 9:
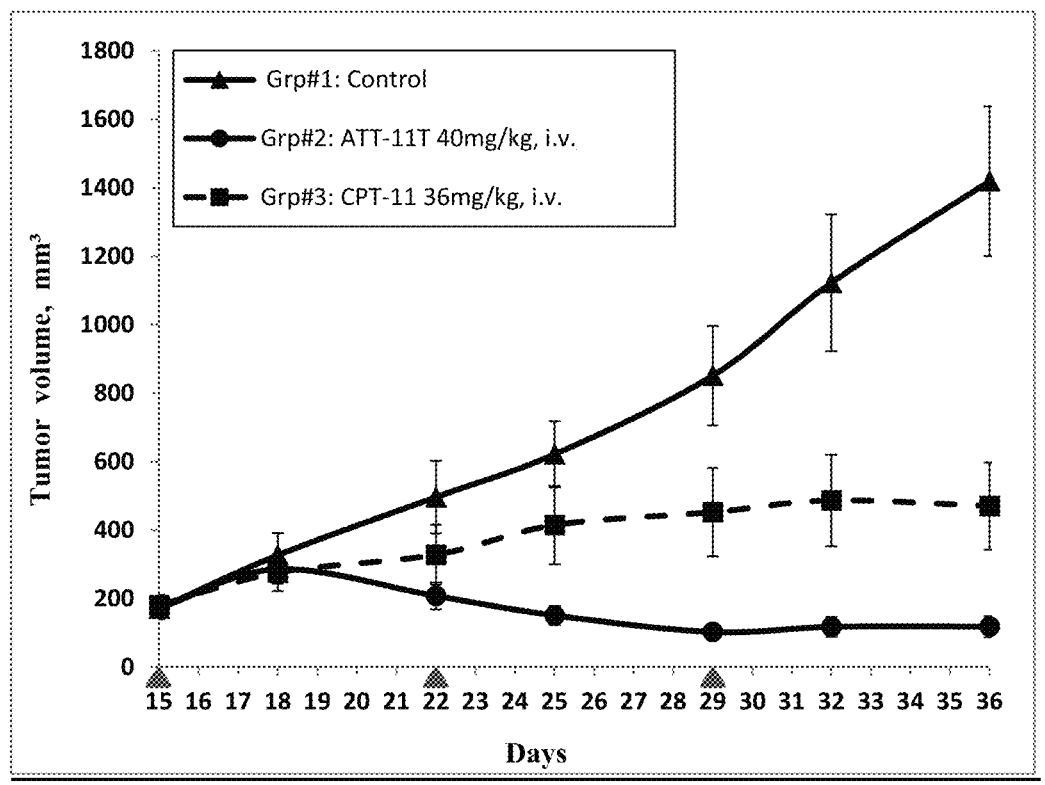

FIG. 9 presents the tumor volumes (lung carcinoma) in mm³ vs days after tumor inoculation, dependent on the treatment (or no treatment) provided. The triangular marks on the X axis indicate days on which the drug was administered.

Figure 10A:
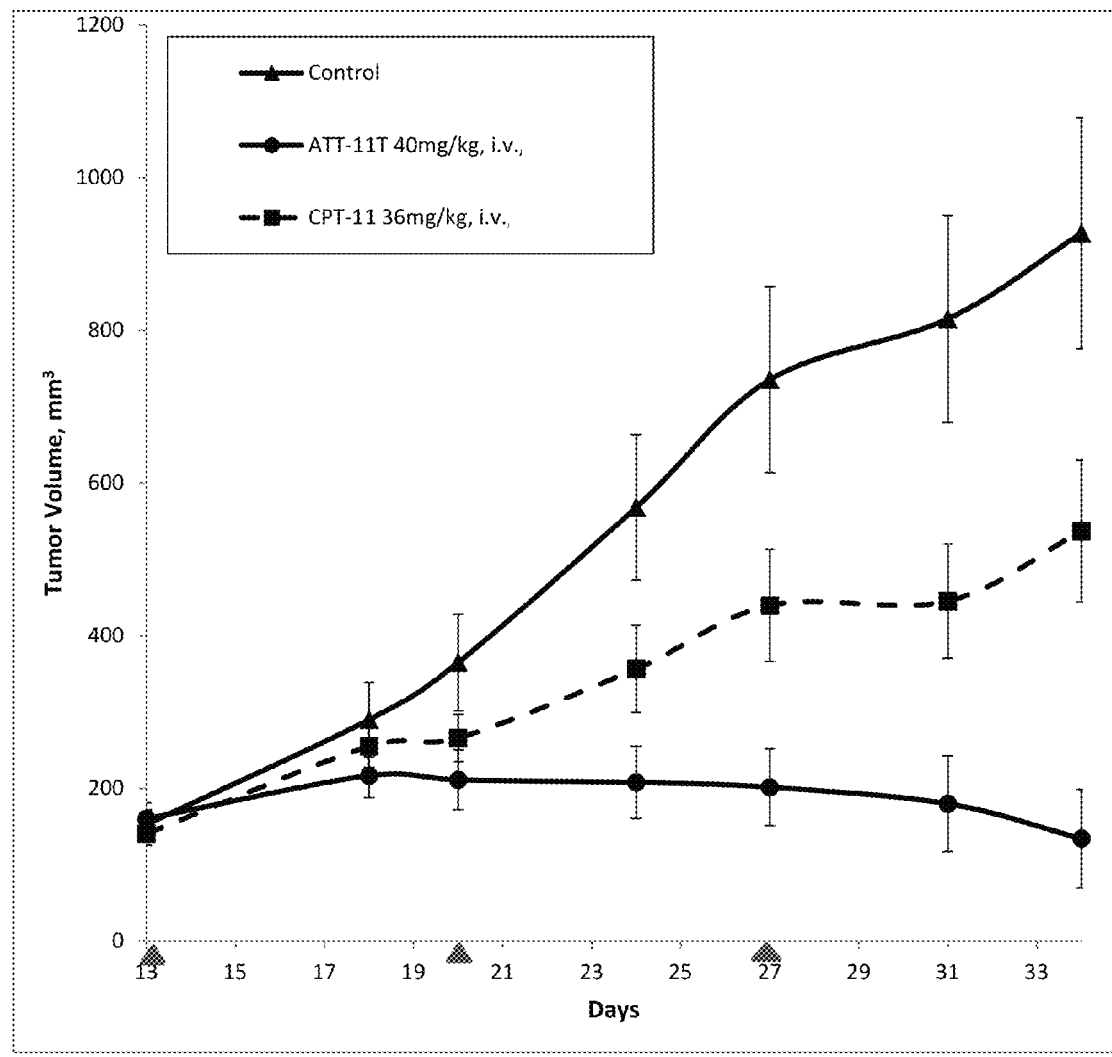

FIG. 10A presents the tumor volumes (pancreatic carcinoma) in mm³ vs days after tumor inoculation, dependent on the treatment (or no treatment) provided; The triangular marks on the X axis indicate days on which the drug was administered.

Figure 10B:
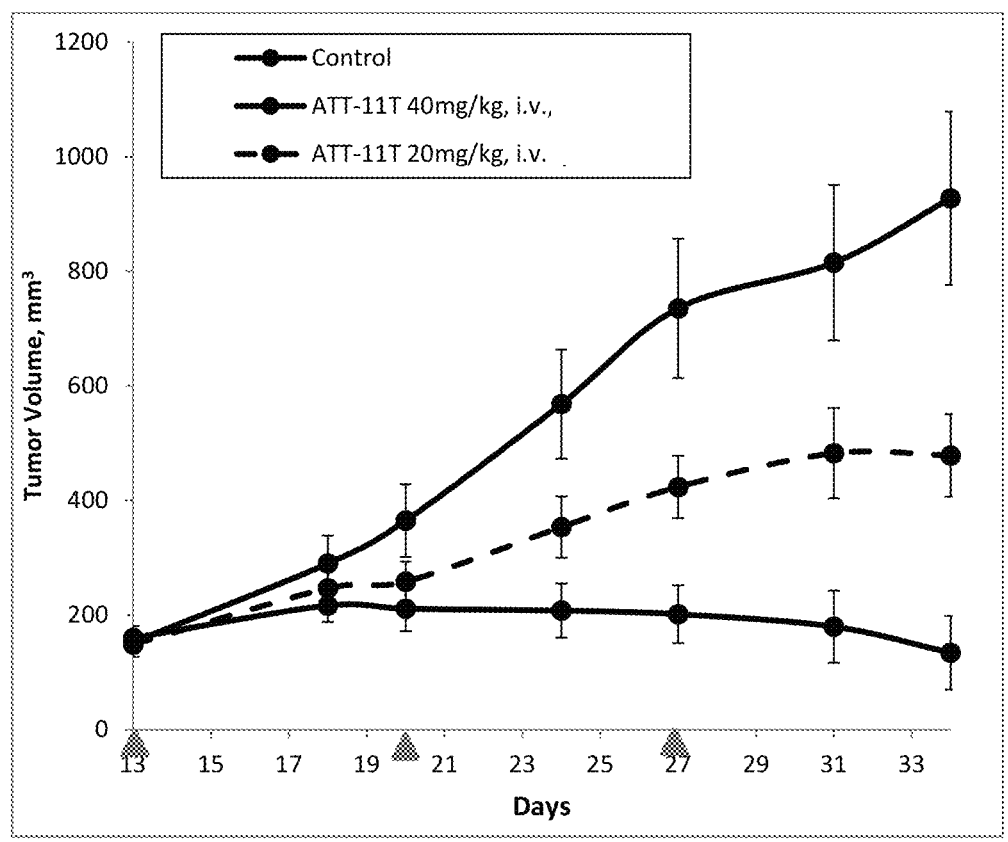

FIG. 10B shows the tumor (pancreatic carcinoma) volume in (mm³) vs. days after tumor inoculation and the treatment with two different doses of ATT11T. The triangular marks on the X axis indicate days on which the drug was administered.

Figure 11A:
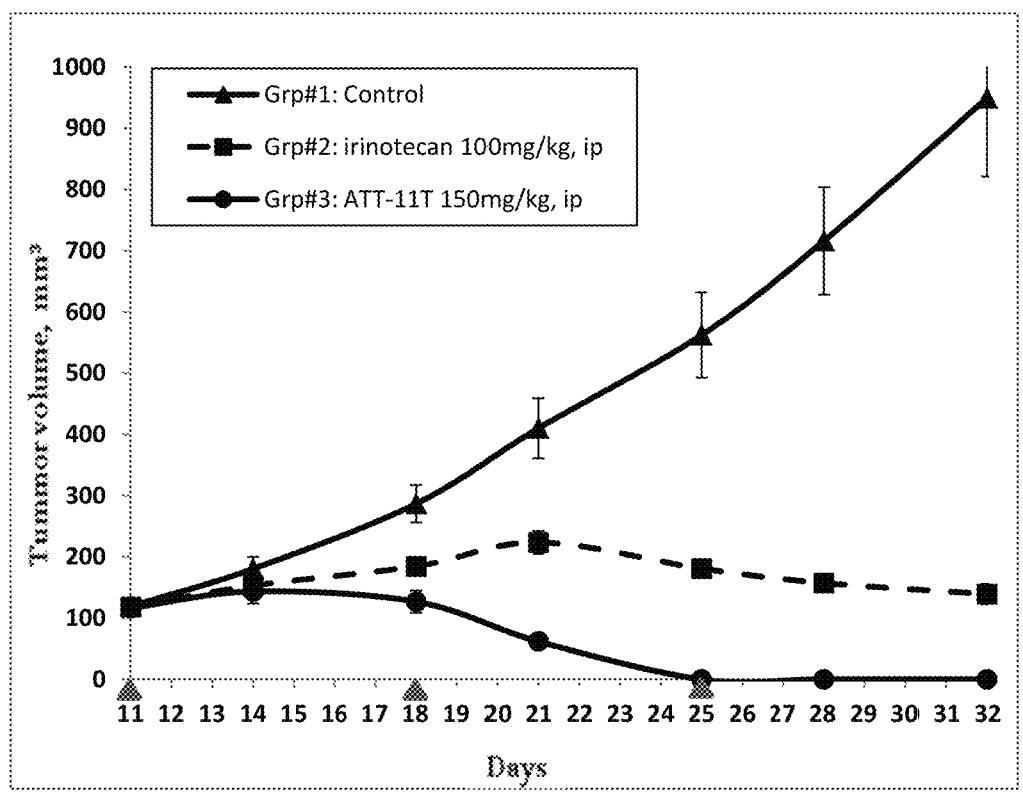
Figure 11B:
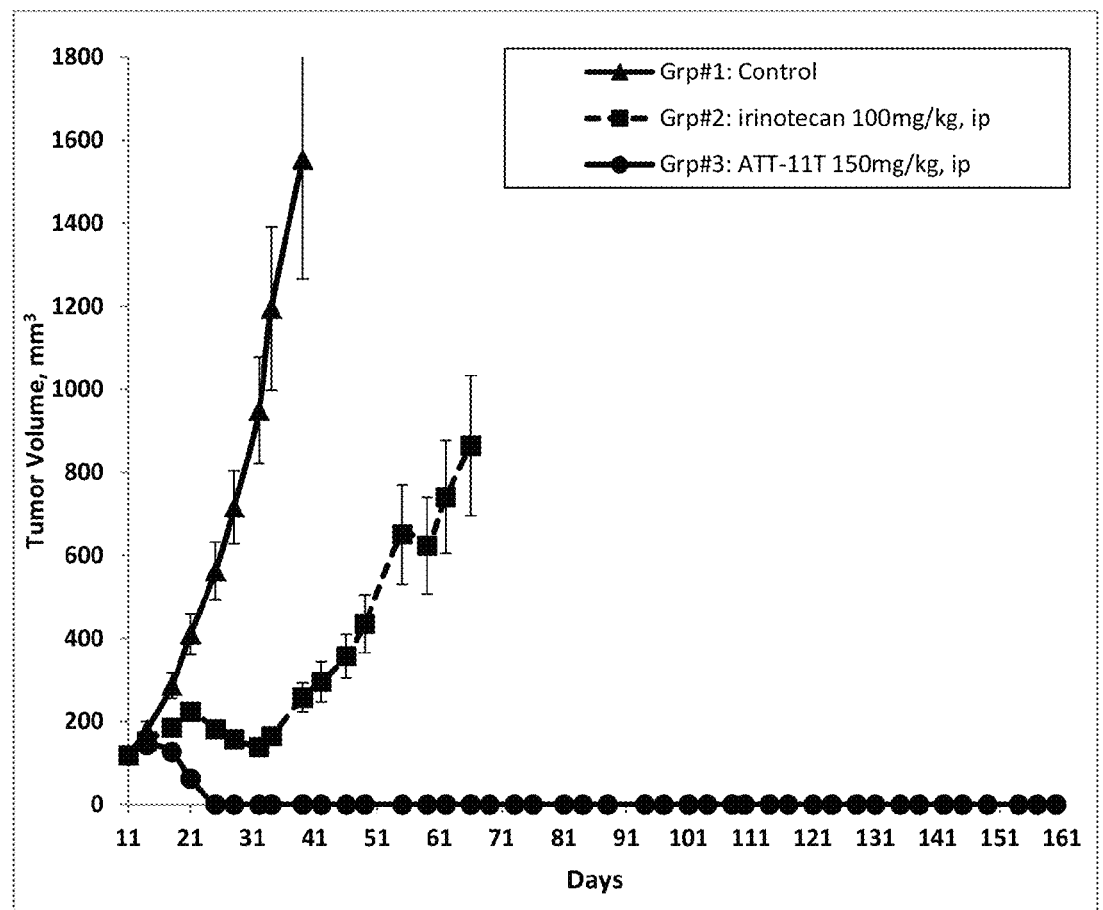

FIGS. 11A and 11B present the tumor volumes (colorectal carcinoma) in mm³.vs. days after tumor inoculation, dependent on the treatment (or no treatment) provided. The triangular marks on the X axis in FIG. 11A indicate days on which the drug was administered.

Figure 12A:
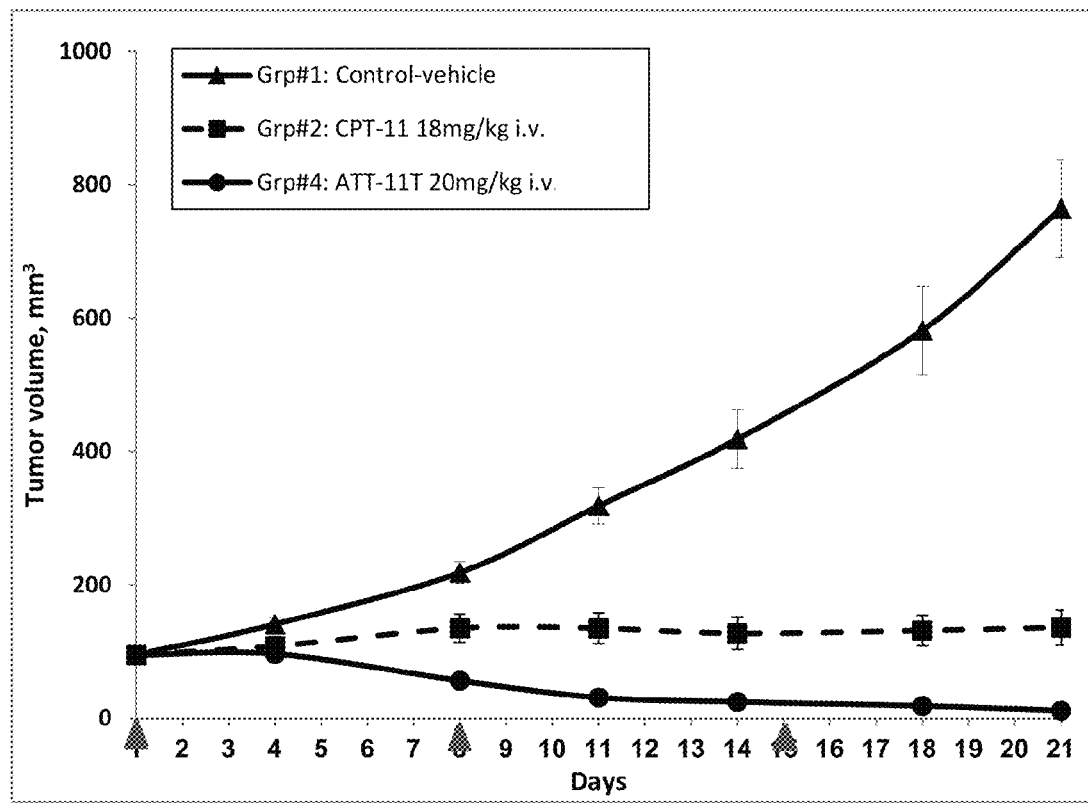
Figure 12B:
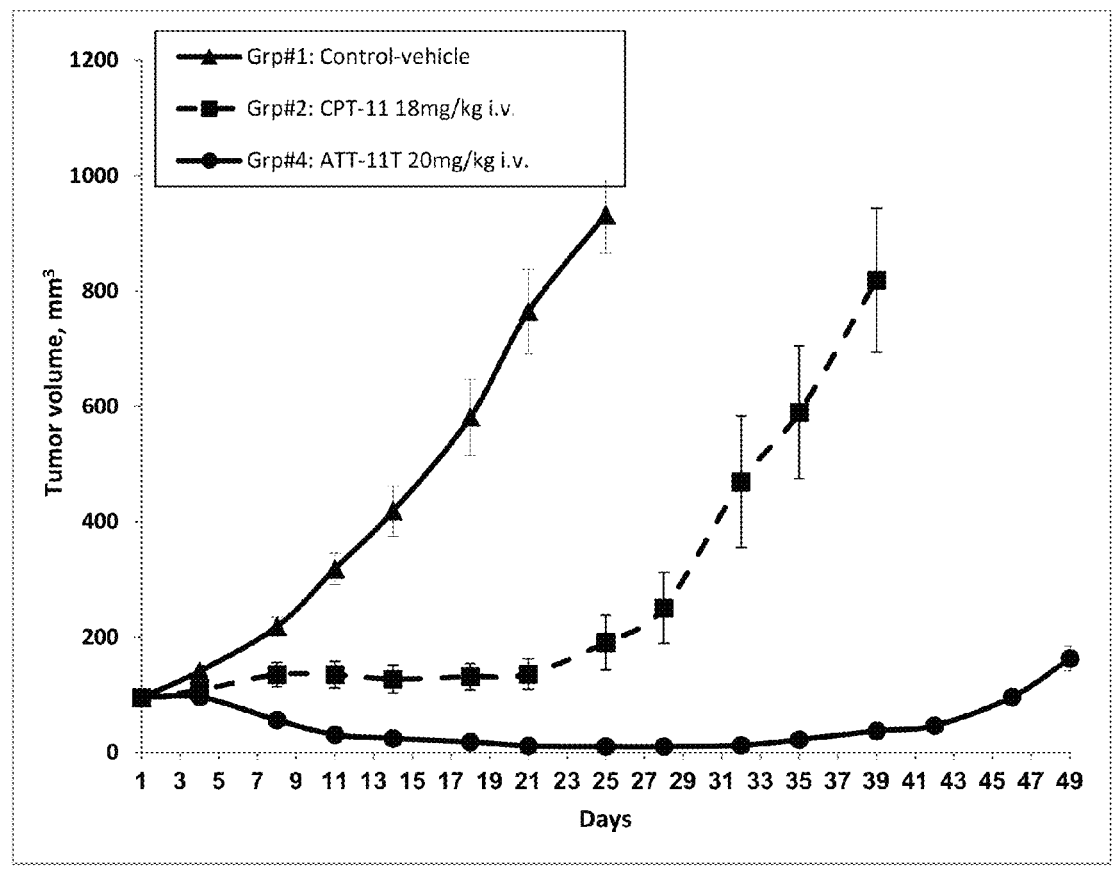

FIGS. 12A and 12B present the tumor volumes (ovarian carcinoma) in mm³ vs days after tumor inoculation, dependent on the treatment (or no treatment) provided. The triangular marks on the X axis in FIG. 11A indicate days on which the drug was administered.

DETAILED DESCRIPTION OF THE INVENTION

In one embodiment there is provided a compound represented by the structure of Formula (I):

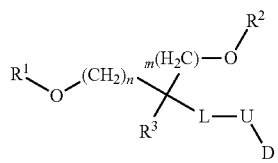

Formula (I)

in which $R^1$ and $R^2$ are the same or different, each being independently selected from $C_1, C_2, C_3, C_4, C_5, C_6, C_7$ or $C_8$ linear, branched or cyclic alkyl, aryl or heteroaryl;

$R^3$ is selected from hydrogen, $C_1, C_2, C_3, C_4, C_5, C_6, C_7$ or $C_8$ linear or branched alkyl;

L is selected from $C_1, C_2, C_3, C_4, C_5, C_6, C_7$ or $C_8$ linear, branched or cyclic alkyl, $C_1, C_2/C_3, C_4, C_5, C_6, C_7$ or $C_8$ linear, branched or cyclic alkyl-amine, aryl, heteroaryl or a combination thereof;

U is selected from —O—; —(CO)O—; —O(CO)—NH—; or —(CO)—NH—;

n and m are integers, each being independently selected from 0,1,2,3,4; and

D is a drug.

According to one embodiment, n=1 and m=1.

According to one embodiment $R^1$ and $R^2$ are each a tert-butyl group, [i.e. —C(CH₃)₃], and the compound is represented by the structure of Formula (II):

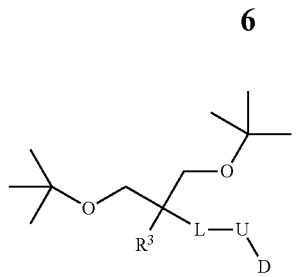

Formula (II)

According to one embodiment $R^3$ is a methyl.

According to another embodiment, there is provided a compound represented by the structure of Formula (III):

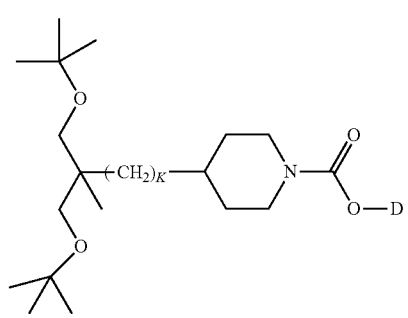

Formula (III)

in which k is an integer of 1, 2, 3, 4, or 5.

According to another embodiment there is provided a compound represented by the structure of Formula (IV):

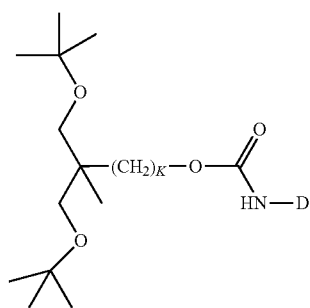

Formula (IV)

in which k is an integer of 1, 2, 3, 4, or 5.

According to another embodiment there is provided a compound represented by the structure of Formula (V):

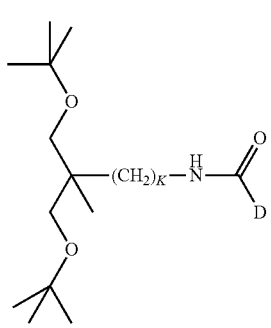

Formula (V)

in which k is an integer of 1, 2, 3, 4, or 5.

According to one embodiment k is 5 and D is either ibuprofen or levodopa.

According to one embodiment there is provided a compound represented by the structure of Formula (VI):

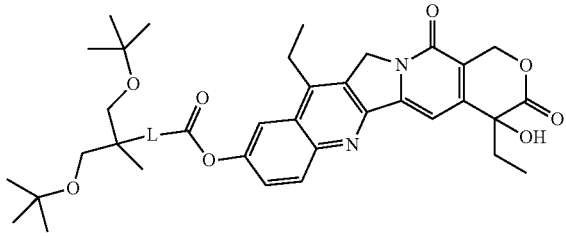

Formula (VI)

in which L is as defined above.

According to one embodiment there is provided a compound represented by the structure of Formula (VII):

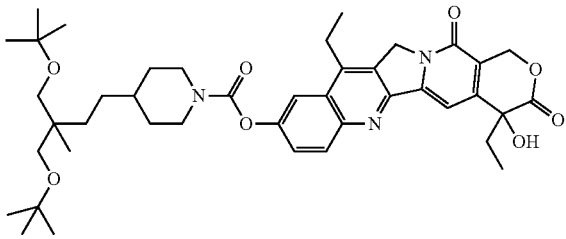

Formula (VII)

The compound of Formula VII is designated ATT-11T.

According to another embodiment there is provided a compound represented by the structure of Formula (VIII):

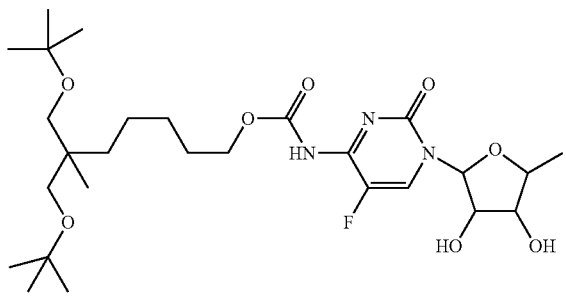

Formula (VIII)

The compound of Formula (VIII) is designated ATT-20.

Embodiments of the invention also provide pharmaceutically acceptable salts, hydrates, solvates and metal chelates of any of the compounds of Formulae I, II, III, IV, V, VI, VII, or VIII, and pharmaceutical compositions containing the compound.

According to some embodiments D is an anti-cancer drug. For example, D can be an inhibitor of topoisomerase, such as camptothecin or derivatives or analogues thereof (for example in Formulae VI and VII); or 5-fluorouracil or analogues thereof, such as capecitabine (for example, in Formula VIII).

According to some embodiments of the invention, D may be an anti-inflammatory drug, a drug for the treatment of immune-mediated disorders, a drug for the treatment of infectious disorders, a drug for the treatment of vascular disorders, a drug for the treatment of toxic disorders, a drug for the treatment of neurological disorders, or a drug for the treatment of psychiatric disorders.

According to some embodiments there is provided a compound, comprising the structure as set forth in Formula IX:

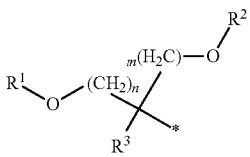

Formula (IX)

in which $R^1$ and $R^2$ are the same or different, each being independently selected from $C_1$, $C_2$, $C_3$, $C_4$, $C_5$, $C_6$, $C_7$ or $C_8$ linear, branched or cyclic alkyl, aryl or heteroaryl; $R^3$ is selected from hydrogen, $C_1$, $C_2$, $C_3$, $C_4$, $C_5$, $C_6$, $C_7$ or $C_8$ linear or branched alkyl; n and m are integers, each being independently selected from 0,1,2,3,4; and * stands for a linkage point to a drug, either directly or through a linker L, as defined above.

According to one embodiment, $R^1$ and $R^2$ are each a tert-butyl group.

According to one embodiment, n=1 and m=1.

According to one embodiment $R^3$ is $CH_3$.

According to one embodiment, there is provided a compound, comprising the structure as set forth in Formula X:

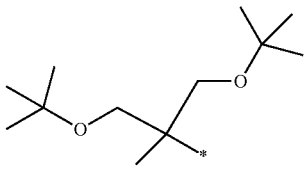

Formula (X)

wherein * stands for a linkage point to a drug, either directly or through a linker L, as defined above.

According to some embodiments, the compounds comprising the structures of Formulae (IX) or (X) may be used in the preparation of a medicament, for example, in the preparation of an anti-cancer drug.

According to some embodiments, the compounds of Formulae (IX) or (X) may be used in the preparation of a conjugate, which optionally includes a linker connecting the compound of Formulae IX or X to a drug.

According to some embodiments of the invention, there is provided a method for the treatment of medical disorders, the method comprising administering to a subject having a medical disorder a therapeutically effective dose of any of the compounds represented by Formulae I, II, III, IV, V, VI, VII or VIII, wherein D is a drug, useful for the treatment of said medical disorder.

According to an embodiment of the invention, said medical disorder is cancer.

Compounds according to embodiments of the invention all have the common feature represented by Formula IX and more specifically, according to some embodiments, the compounds have the common feature represented by Formula X, which provides improved efficacy and drug performance in parameters such as oral bioavailability, selectivity and an improved pharmacokinetic profile.

In one embodiment of the invention, the conjugate having the structure set forth in Formula (VII) and designated ATT-11T comprises the anti-cancer drug SN-38.

ATT-11T is a carbamate pro-drug of the anti-cancer agent SN-38. Upon cleavage of the carbamate bond by esterases in the body, SN-38 is released to exert its cytotoxic effect through inhibition of the enzyme topoisomerase I.

In another embodiment of the invention, the conjugate having the structure set forth in Formula (VIII) and designated ATT-20T, comprises the anti-cancer drug capecitabin.

Embodiments of the invention provide a method for treatment of disease, by administering to the subject having the disease a compound, a therapeutically effective amount of conjugate or a pharmaceutical composition comprising any one of the compounds set forth in Formulae I, II, III, IV, V, VI, VII or VIII.

The compounds of the invention can be active as therapeutic agents by themselves, i.e., without any further structural modifications, or may act as pro-drugs, i.e., capable of exerting a pharmacological action only after metabolic conversion in the body. Among others, said conversion can be enzymatic cleavage of the molecule of the invention at the respective ester, amide or carbamate moieties, as applicable for the specific compound.

In an embodiment of the invention there is provided a method for treatment of medical disorders, wherein said medical disorder are selected from cancer, inflammatory disorders, immune-mediated disorders, infectious disorders, vascular disorders, toxic disorders, neurological disorders, or psychiatric disorders.

Embodiments of the invention provide a pharmaceutical composition comprising a compound or conjugate according to any of Formulae I, II, III, IV, V, VI, VII or VIII, as described above and/or as described in the Examples below, and pharmaceutically acceptable salts, hydrates and solvates thereof and solvates and hydrates of the salts.

Some examples of salts include nontoxic alkaline metal salts, alkaline earth metal salts and ammonium salts such as sodium, potassium, lithium, calcium, magnesium, barium and ammonium salts. In addition, nontoxic acid addition salts are also included in the above-mentioned salts, for example, hydrochlorides, hydrogen chlorides, hydrogen bromides, sulfates, bisulfates, acetates, oxalates, valerates, oleates, laurates, borates, benzoates, lactates, malates, p-toluene sulfonates (tosylates), citrates, maleates, fumarates, succinates, tartrates, sulfonates, glycolates, maleates, ascorbates and benzene sulfonates.

Pharmaceutical compositions according to embodiments of the invention may include a pharmaceutically accepted carrier such as a diluent, adjuvant, excipient, or vehicle with which the therapeutic agent is administered. Some examples of pharmaceutically acceptable carriers include water, salt solutions, alcohol, silicone, waxes, petroleum jelly, vegetable oil, peanut oil, soybean oil, mineral oil, sesame oil, polyethylene glycols, propylene glycol, liposomes, sugars, gelatin; lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

The pharmaceutical compositions may be manufactured, for example, by means of conventional mixing, dissolving, granulating, levitating, emulsifying, encapsulating, entrapping, lyophilizing processes or other suitable processes.

The pharmaceutical compositions can take the form of solutions, suspensions, emulsions, tablets, pills, capsules, powders, sustained-release Formulations and the like, depending on the intended route of administration. Examples of routes of administration include parenteral, e.g., intravenous, intramuscular, subcutaneous, intra-arterial, intraportal, intrathecal, intradermal, transdermal (topical), transmucosal, intra-articular, intraperitoneal, and intrapleural, as well as intrathecal, intracerebral, inhalation and pulmonary administration. In another aspect, the delivery system and pharmaceutical composition are administered to the subject locally, for example, by injection to a local blood vessel which supplies blood to a particular tumor, organ, tissue, or cell afflicted by disorders or diseases.

For example, for parenteral administrations, the composition may comprise one or more of the following components: a sterile diluent such as water for injection, saline solution; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

For example, for injection, the conjugates of the invention may be Formulated in aqueous solutions, preferably in physiologically compatible buffers such as physiological saline buffer. The solution may contain Formulatory agents such as suspending, stabilizing and/or dispersing agents. In a preferred embodiment, the delivery systems are formulated in sterile aqueous solutions.

For example, for intravenous administration, suitable carriers include physiological saline, bacteriostatic water, or phosphate buffered saline (PBS). In all cases, the composition must be sterile and, when injected, should be fluid to the extent that easy injectability with a syringe. Compositions may include preservatives such as, parabens, chlorobutanol, phenol, ascorbic acid, thimerosal, and the like.

The pharmaceuticals according to embodiments of the invention can be administered orally, for example in the form of pills, tablets, lacquered tablets, sugar-coated tablets, granules, hard and soft gelatin capsules, aqueous, alcoholic or oily solutions, syrups, emulsions or suspensions. For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc. In one embodiment, the medicament, together with one or more auxiliary excipient materials may be compressed into a tablet form such as a single layer or multilayer tablet. Tablets according to embodiments of the invention can optionally be coated with a controlled release polymer so as to provide additional controlled release properties.

For example, for administration by inhalation, the delivery systems may be formulated as an aerosol spray from pressurized packs or a nebulizer, with the use of a suitable propellant, e.g., dichlorodifluoromethane, trichlorofluoromethane, dichlorotetrafluoroethane, carbon dioxide or other suitable gas.

Various doses can be used, and doses may be administered in various intervals, according to the disease, the clinical status of the patient or concomitant medications. Dosage can vary, according to the clinical judgment of the physician.

Embodiments of the invention provide methods for treatment of medical disorders. According to an embodiment of the invention, one method comprises administering to a subject (human or animal) a therapeutically effective dose of a compound or a pharmaceutical composition according to any of the Formulae I, II, III, IV, V, VI, VII or VIII. Said compound or pharmaceutical composition may be administered with additives, such as those described above, and administration may take any suitable route, such as those described above.

In one aspect of the invention, the compound according to any of Formulae I, II, III, IV, V, VI, VII or VIII has anti-cancer activity, i.e. is capable of causing damage to and/or killing tumor cells, either by itself, or upon its cleavage to an active metabolite. According to this aspect of the invention, said compound or related pharmaceutical composition may be used for the treatment of cancer, wherein the tumor(s) may involve or originate from any organ in the body.

In one embodiment, the types of cancer to be treated by the compounds of the invention and/or their related pharmaceutical compositions include primary or secondary tumors of the pancreas, lung, colon, breast, melanoma, lymphoma, prostate, thyroid, testes, ovary, skin, brain or bone.

In another aspect of the invention, the compound according to any of Formulae I, II, III, IV, V, VI, VII or VIII comprises a drug that is useful for the treatment of a medical disorder, selected from inflammatory disorders, immune-mediated disorders, infectious disorders, vascular disorders, toxic disorders, psychiatric disorders or neurological disorders. According to this aspect of the invention, a compound or related pharmaceutical composition of the invention may be used for the treatment of the respective medical disorder.

According to some embodiments of the invention, the compounds or their related pharmaceutical compositions may be used as monotherapy, i.e., as a single chemotherapeutic agent, or in combination with other therapeutic agents, i.e., as part of a combination therapy. Treatment can be acute or chronic.

Some examples will now be described, in order to further demonstrate the invention, and to exemplify how embodiments of the invention may be carried-out in practice. The examples illustrate, in a non-limiting manner, an exemplary method for the preparation of a compound according to one embodiment of the invention, and biological performance in tumor inhibition, both in vitro and in vivo, in xenograft animal models of cancer. In addition, a favorable pharmacokinetic profile of a compound of the invention is demonstrated, as examined in beagle dogs.

EXAMPLES

Example 1

An exemplary method for preparation of the compound designated ATT-11T is demonstrated. However, modifications of this method (e.g., similar processes including additional or other steps known in the art such as alkylation, hydration, condensation, as well as other steps), which may result in similar compounds, are also included in embodiments of the invention.

The synthetic scheme for ATT-11T according to one embodiment of the invention is illustrated below. As a first step, Boc protection is preformed on a piperidine derivative 1, followed by bromination to obtain compound 3, and condensation with diethyl-methyl malonate, which is produced by methylation of di-ethyl malonate 4. Said condensation results in compound 6A, which is then reduced, to obtain compound 6B. Subsequently, etherification is performed, in order to obtain compound 7. Compound 7 is then Boc-de-protected and condensed with SN-38 (compound 10), to result in compound 11, i.e., the desired product ATT-11T. This synthetic route is further illustrated in the following synthetic scheme:

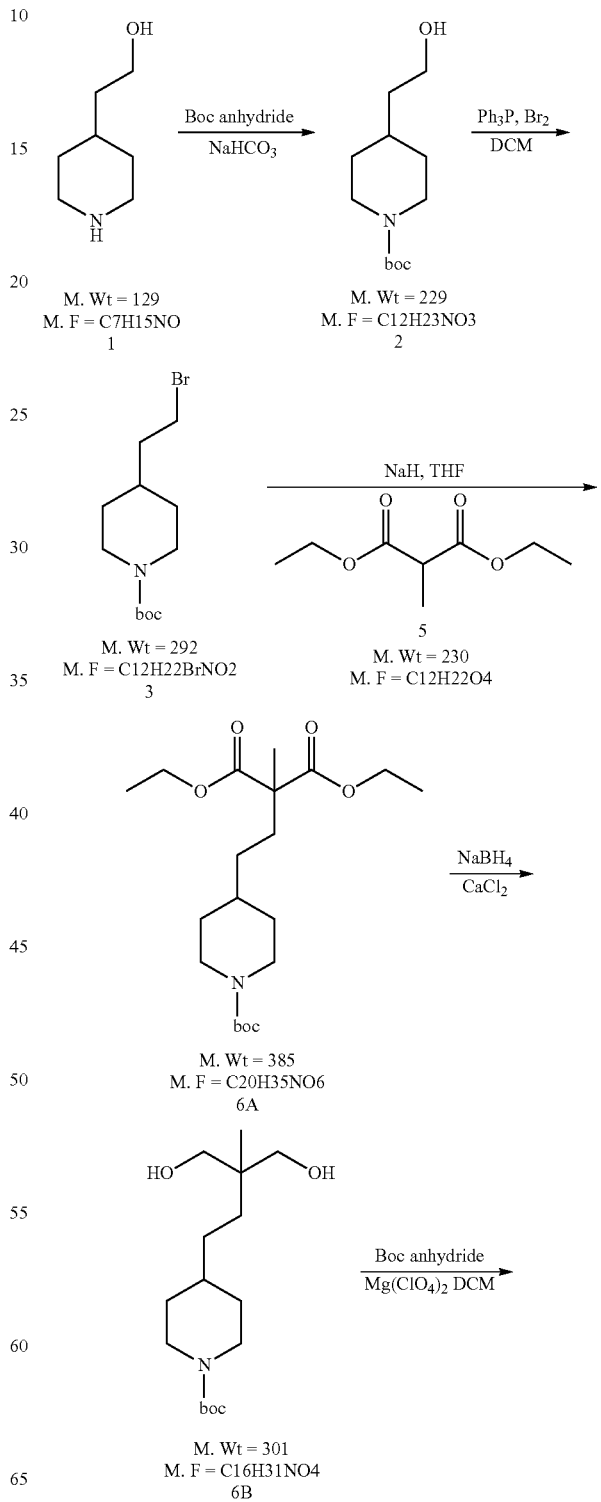

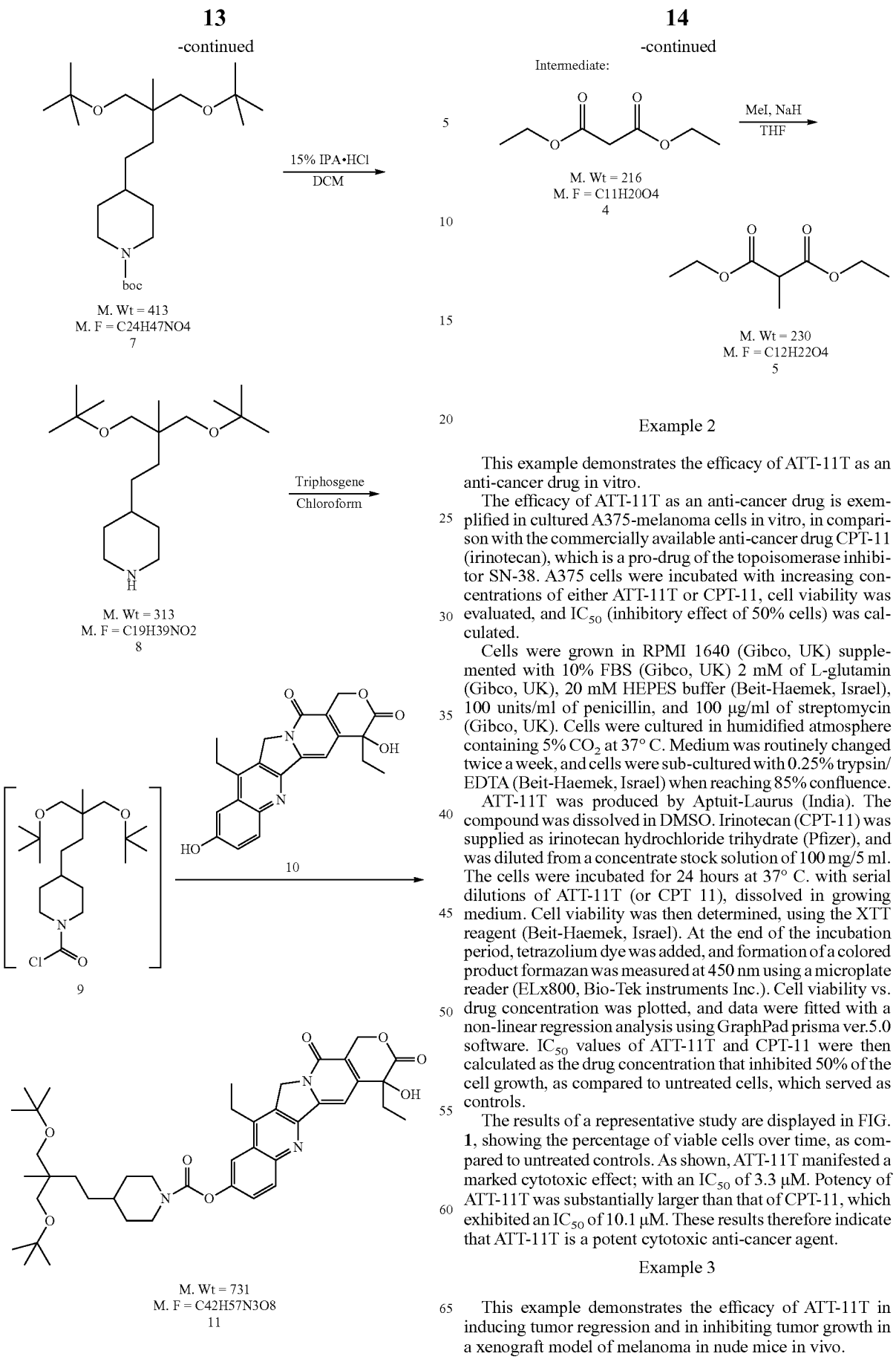

Example 2

This example demonstrates the efficacy of ATT-11T as an anti-cancer drug in vitro.

The efficacy of ATT-11T as an anti-cancer drug is exemplified in cultured A375-melanoma cells in vitro, in comparison with the commercially available anti-cancer drug CPT-11 (irinotecan), which is a pro-drug of the topoisomerase inhibitor SN-38. A375 cells were incubated with increasing concentrations of either ATT-11T or CPT-11, cell viability was evaluated, and $IC_{50}$ (inhibitory effect of 50% cells) was calculated.

Cells were grown in RPMI 1640 (Gibco, UK) supplemented with 10% FBS (Gibco, UK) 2 mM of L-glutamin (Gibco, UK), 20 mM HEPES buffer (Beit-Haemek, Israel), 100 units/ml of penicillin, and 100 µg/ml of streptomycin (Gibco, UK). Cells were cultured in humidified atmosphere containing 5% $CO_2$ at 37° C. Medium was routinely changed twice a week, and cells were sub-cultured with 0.25% trypsin/EDTA (Beit-Haemek, Israel) when reaching 85% confluence.

ATT-11T was produced by Aptuit-Laurus (India). The compound was dissolved in DMSO. Irinotecan (CPT-11) was supplied as irinotecan hydrochloride trihydrate (Pfizer), and was diluted from a concentrate stock solution of 100 mg/5 ml. The cells were incubated for 24 hours at 37° C. with serial dilutions of ATT-11T (or CPT 11), dissolved in growing medium. Cell viability was then determined, using the XTT reagent (Beit-Haemek, Israel). At the end of the incubation period, tetrazolium dye was added, and formation of a colored product formazan was measured at 450 nm using a microplate reader (ELx800, Bio-Tek instruments Inc.). Cell viability vs. drug concentration was plotted, and data were fitted with a non-linear regression analysis using GraphPad prisma ver.5.0 software. $IC_{50}$ values of ATT-11T and CPT-11 were then calculated as the drug concentration that inhibited 50% of the cell growth, as compared to untreated cells, which served as controls.

Figure 1:
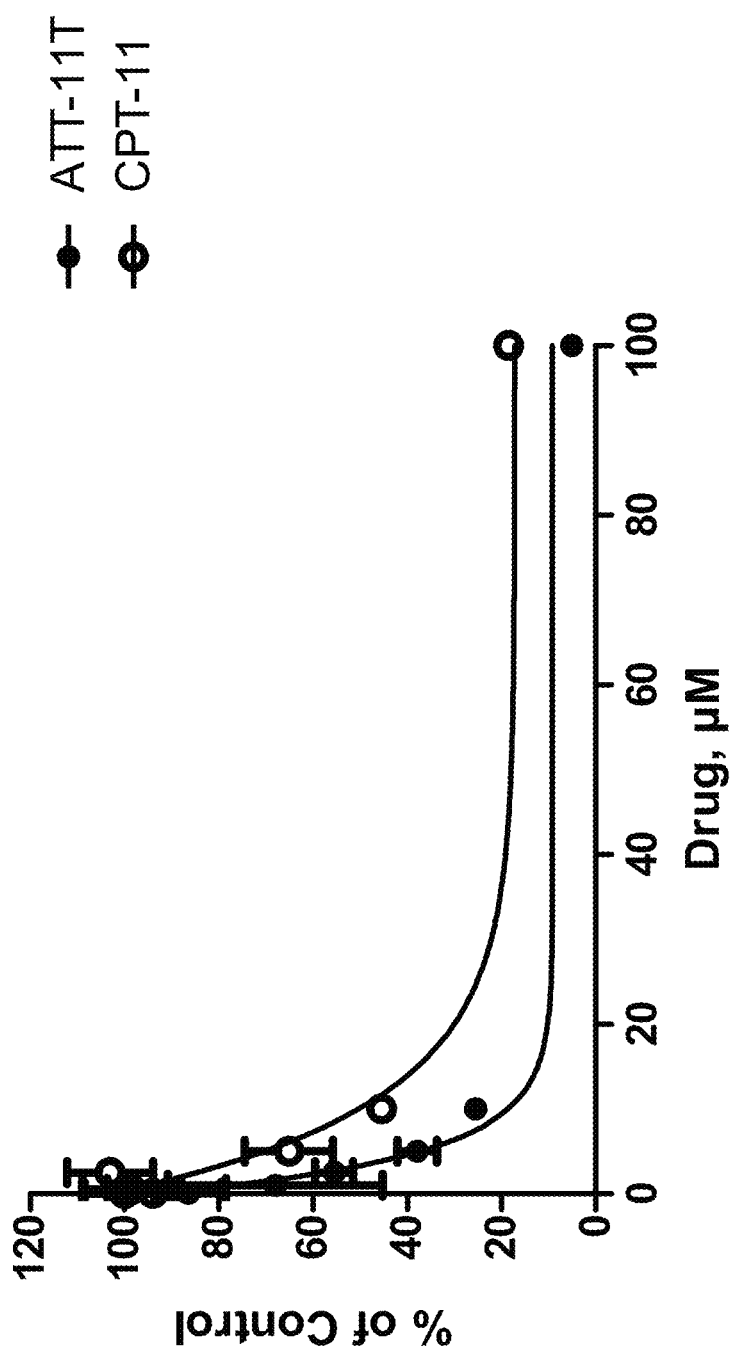
FIG. 1 shows the efficacy of ATT-11T (a compound according to an embodiment of the invention) as a cytotoxic anticancer drug, as exemplified in cultured A375-melanoma cells in vitro, in comparison with the anti-cancer drug CPT-11 (irinotecan), which is a pro-drug of SN-38, an anti-cancer agent, active as an inhibitor of the enzyme topoisomerase I. A375 cells were incubated with increasing concentrations of ATT-11T or CPT-11, and cell viability was assessed. The cytotoxic effect of these agents was expressed as the percentage of viable cells at 24 hours of incubation. ATT-11T exhibited potent cytotoxic effect, with $IC_{50}$ (inhibitory concentration of 50% of cells) of 3.3 μM, being more potent than CPT-11. Therefore, as shown, ATT-11T is a potent anti-cancer agent.

The results of a representative study are displayed in FIG. 1, showing the percentage of viable cells over time, as compared to untreated controls. As shown, ATT-11T manifested a marked cytotoxic effect; with an $IC_{50}$ of 3.3 µM. Potency of ATT-11T was substantially larger than that of CPT-11, which exhibited an $IC_{50}$ of 10.1 µM. These results therefore indicate that ATT-11T is a potent cytotoxic anti-cancer agent.

Example 3

This example demonstrates the efficacy of ATT-11T in inducing tumor regression and in inhibiting tumor growth in a xenograft model of melanoma in nude mice in vivo.

Subcutaneous A375 melanoma tumors were established in mice by injection of A375 melanoma cells ($0.75 \times 10^6$ per animal per site) into the right flank region of athymic nude mice (female, 8-9 weeks, 10 animals per group). Tumor dimensions were measured with a caliper twice each week and tumor volume ($mm^3$) was calculated using the Formula: $TV=0.52$ $L \times W^2$, where L and W are the major and minor dimensions, respectively. Drug treatment was initiated on day 10, when tumors reached an average volume of 75-100 $mm^3$ ATT-11T was administered intravenously into the tail vein of the mice, in a vehicle comprising 10% DMSO and 10% bovine serum albumin (BSA) in 0.1M sodium phosphate buffer (pH 5.8). The drug was administered at a dose of either 5 or 20 mg/kg, given three times a week for three weeks. Tumor-bearing mice, injected only with the vehicle solution served as controls.

Figure 2:
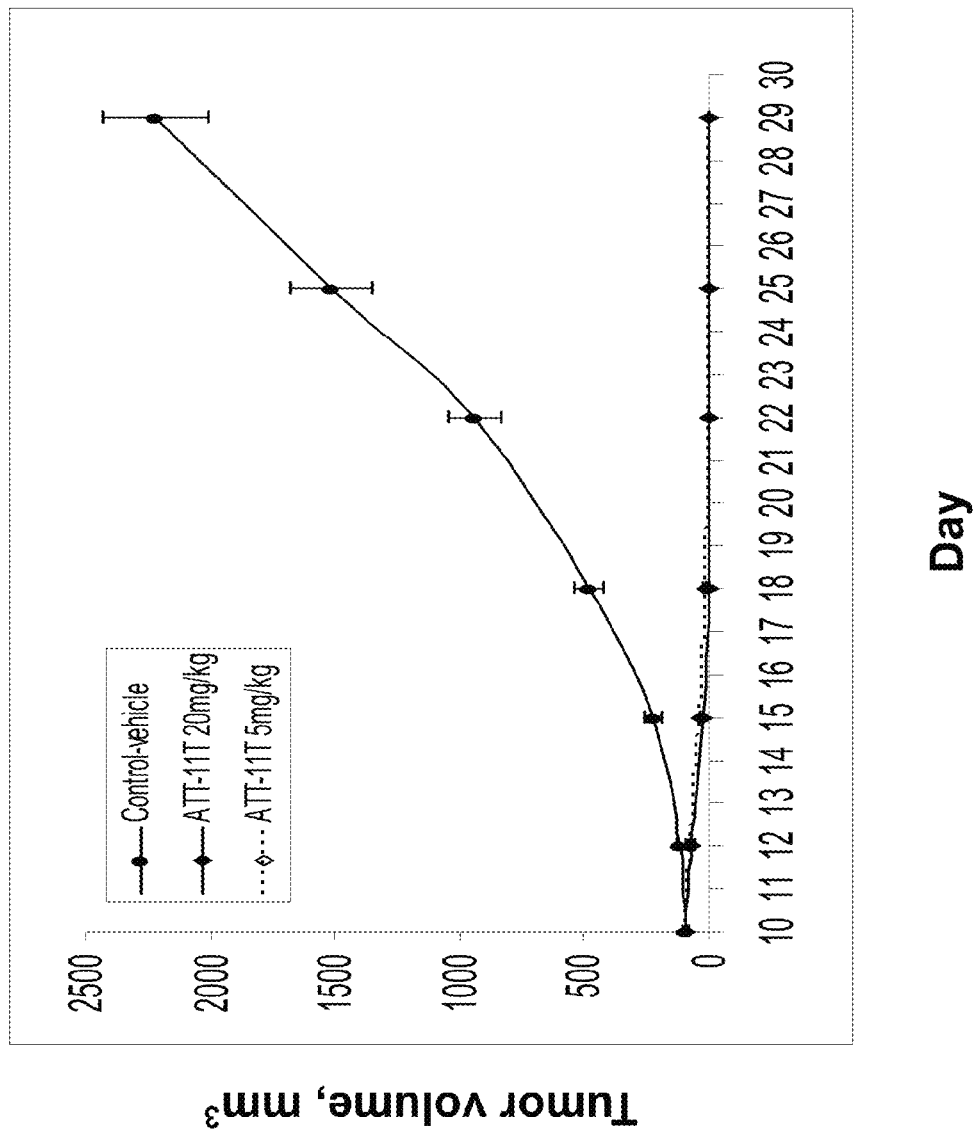
FIG. 2 shows the performance of ATT-11T in inhibiting tumor growth in tumor-bearing nude mice. A375 melanoma tumor-bearing mice were treated with ATT-11T (5 or 20 mg/kg×9), and tumor volumes ($mm^3$) were measured, in comparison with the tumor volumes in control, untreated mice. ATT-11T exerted a dramatic effect on the tumors, with complete tumor regression and growth inhibition, observed with both doses of the drug.

FIG. 2 shows the tumor volume ($mm^3$) vs. days after tumor inoculation. As shown, ATT-11T manifested a dramatic inhibitory effect on tumor growth. While tumors of the control untreated animals manifested rapid growth, ATT-11T caused complete tumor regression and 100% growth inhibition, lasting at one week after the last administration of the drug. This substantial effect of the drug was observed in both dose groups, i.e., 5 mg/kg, and 20 mg/kg.

Figure 3:
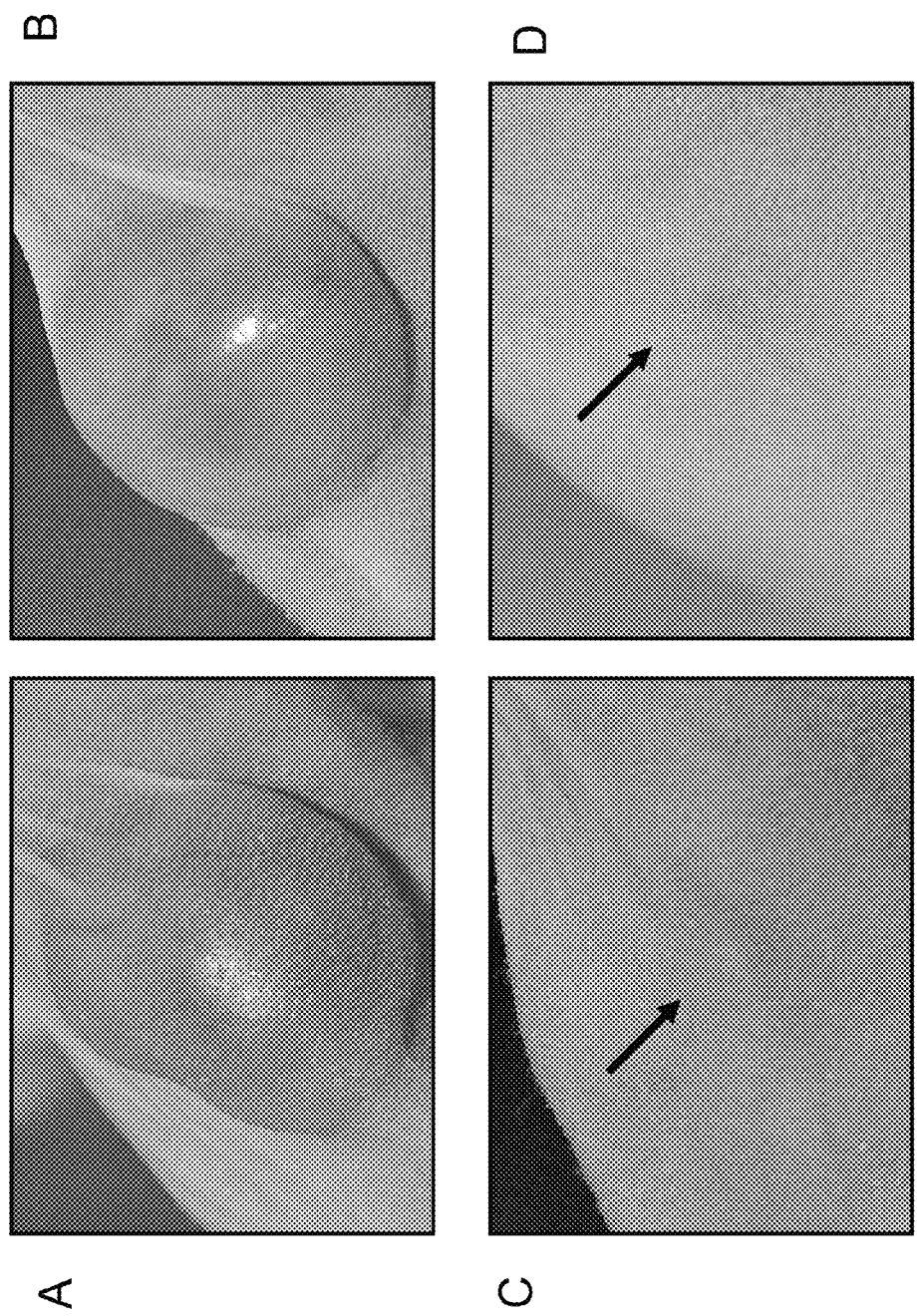
FIG. 3 demonstrates the anti-cancer effect of ATT-11T, causing regression and growth inhibition of melanoma A375 tumors in nude mice. Upper panels (A,B) shows representative tumors from untreated animals, while the lower panels (C,D) show the tumor inoculation sites (arrows) in animals treated with a relatively low dose (5 mg/kg×9) of ATT-11T. As shown, ATT-11T exerted a potent anti-cancer effect, causing tumor regression and tumor growth inhibition.

FIG. 3 (upper panel) demonstrates two representative tumors (A and B) from control untreated mice on day 29 after inoculation (one day after the last administration of the vehicle). Lower panel (C and D) demonstrates the tumor inoculation site (arrows) in two representative mice treated with 5 mg/kg of ATT-11T, on day 29, i.e., one day after the last administration of the drug.

As shown, ATT-11T caused complete tumor regression and tumor growth inhibition, thus demonstrating its potent anti-cancer activity in vivo.

Example 4

This example demonstrates the efficacy of ATT-11T in inducing delay in tumor growth in a xenograft model of melanoma in nude mice in vivo.

The rate of tumor growth following the last dose of chemotherapy was assessed for ATT-11T, in comparison with that of CPT-11 (irinotecan). Drugs, i.e., ATT-11T or CPT-11 were administered intravenously into the tail vein of A375 melanoma-bearing mice, as described above (10 animals per group). CPT-11 was administered as hydrochloride trihydrate (Pfizer, USA), diluted from a concentrate stock solution of 100 mg/5 ml. ATT11-T (Aptuit-Luarus, India) was administered in a vehicle as described above. Tumor-bearing mice injected only with the vehicle solution served as controls. ATT-11T was administered at a dose of either 5 or 20 mg/kg, given twice a week for three weeks. CPT-11 was administered at a dose of 75 mg/kg, given once a week for three weeks. Tumor volume was evaluated as described above.

Drug-induced delay in tumor growth was assessed by two measures: (i). Tumor volume inhibition (TVI %) at one week after the last treatment in treated versus control tumors, which was calculated according to the Formula TVI (%)=(1-T/C)× 100, where T and C are the tumor volume of the treated and control groups, respectively; and (ii). Tumor growth delay (TGD), assessed as the time period (days) of treatment-induced delay in tumor reaching a pre-determined volume of 3,500 $mm^3$, as compared to the vehicle-treated controls.

Figure 4A:
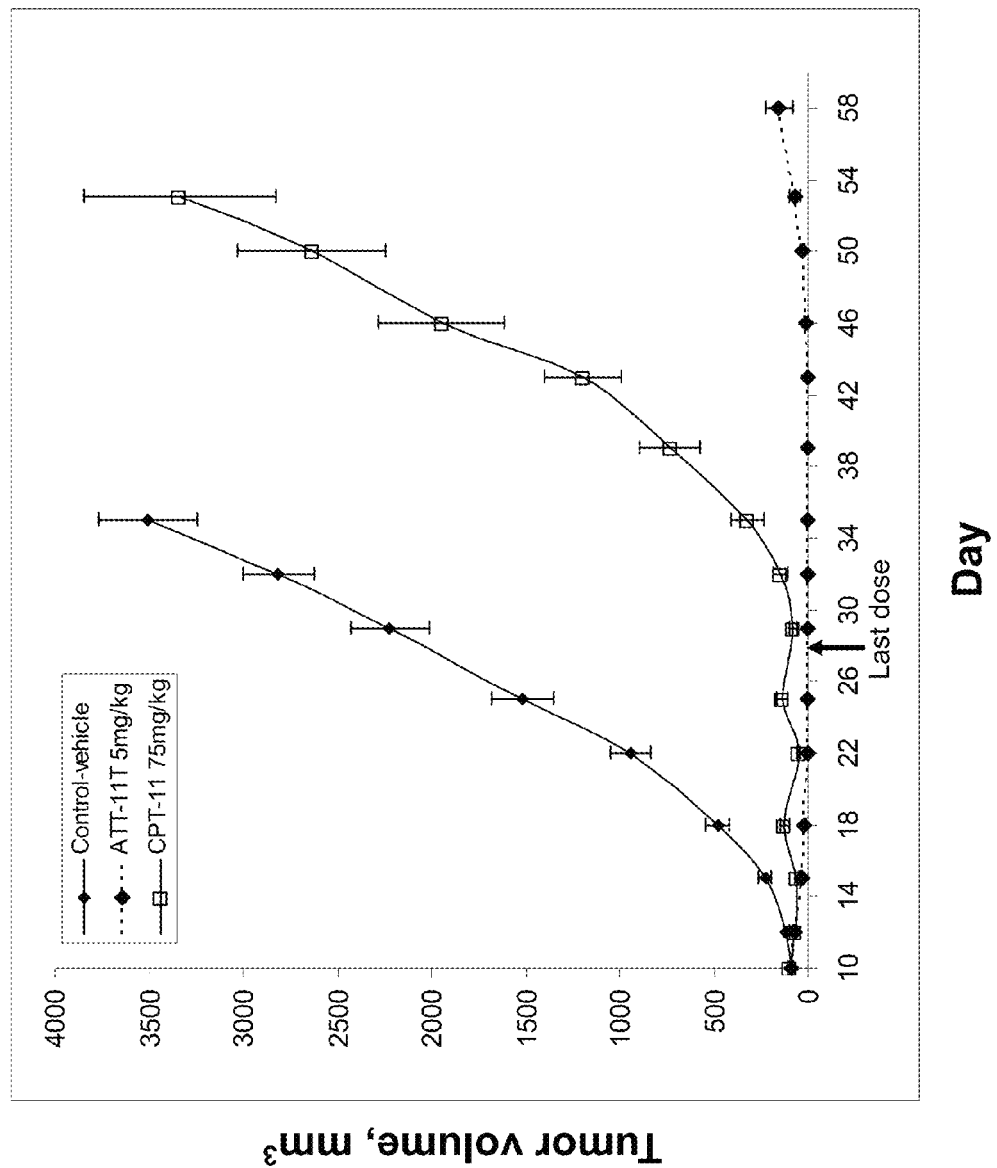
FIGS. 4A and 4B show tumor growth delay, exerted by ATT-11T in melanoma A375 tumor-bearing mice. Tumor-bearing mice were treated with ATT-11T (5 mg/kg or 20 mg/kg×9), or CPT-11 (75 mg/kg×3), and tumor growth was followed for one month after the last dose. As shown, ATT-11T at both doses substantially inhibited tumor growth, even at one month after the last dose, as compared to CPT-11.
Figure 4B:
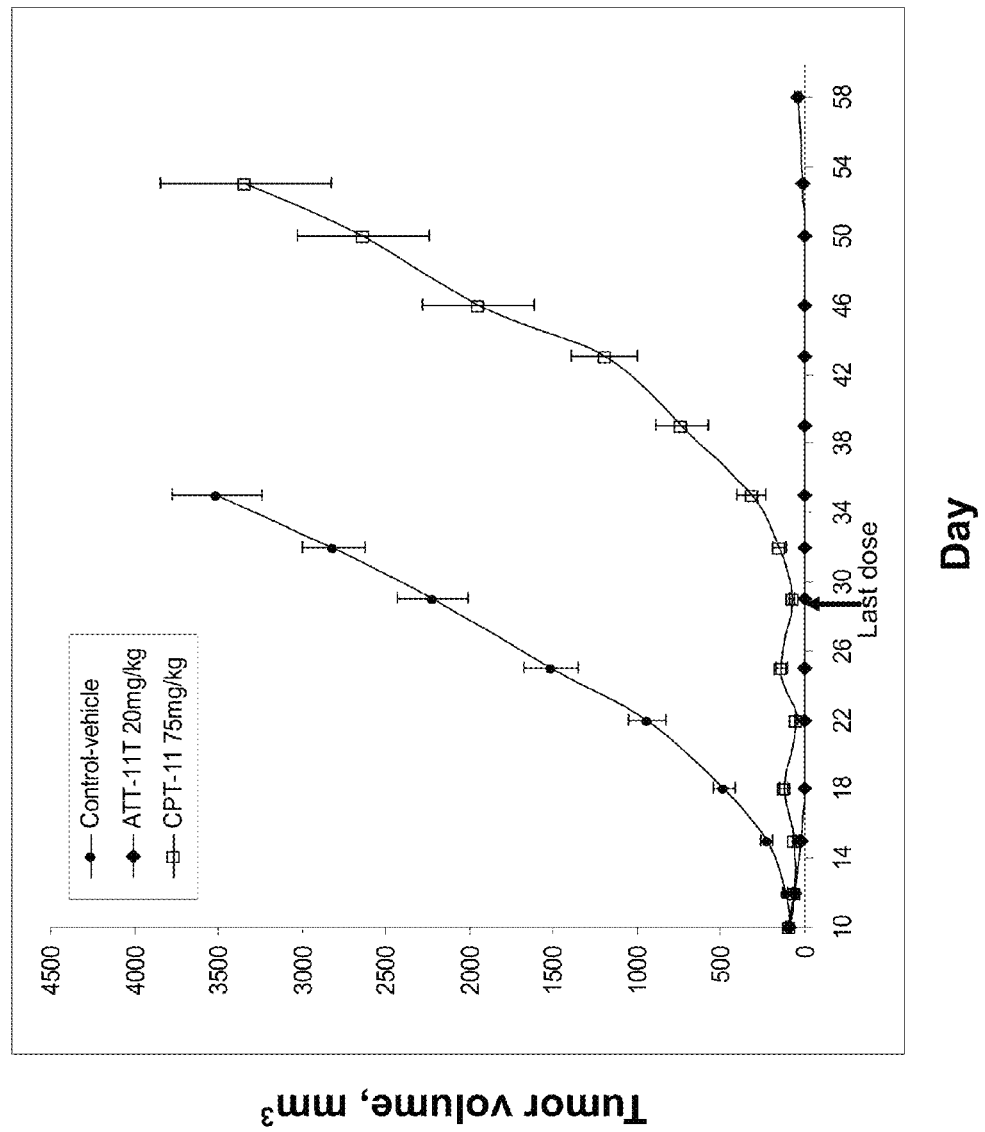

As shown in FIG. 4A and FIG. 4B, both doses of ATT-11T (5 mg/kg or 20 mg/kg, respectively) caused a substantial inhibition of tumor growth, with complete tumor regression, (TVI of 100%) at one week after the last dose of either dose of the drug. While CPT-11 manifested marked tumor inhibition, it never reached the complete tumor regression observed with ATT-11T, and culminated in TVI of 95% at one week after the last dose of the drug.

Assessment of the tumor growth rate 30 days following the last dose of treatment (58 days after tumor cell inoculation) revealed rapid tumor growth in the CPT-11-treated group, starting soon after the administration of the last dose of the drug. Accordingly, the control group and the CPT-11 group reached the endpoint tumor volume of 3,500 $mm^3$ on days 35 and 53 post tumor inoculation, respectively. By contrast, the animals treated with ATT-11T showed little (at the dose of 5 mg/kg, FIG. 4A) or no growth (at the dose of 20 mg/kg, FIG. 4B) even at day 30 after the last dose of the drug.

Taken together, these results indicate that ATT-11T has potent anti-tumor properties, being able to induce both tumor regression and prolonged inhibition of tumor growth.

Example 5

This example evaluates potential adverse effects of ATT-11T in tumor-bearing nude mice For the evaluation of potential adverse effects of ATT-11T, nude mice, bearing the A375 melanoma tumors and treated with ATT-11T as described above, were monitored for adverse effects immediacy after drug administration, and also twice a week, through one day after last dose. The evaluation protocol consisted of gross observation, registration of abnormal signs, and determination of body weight. Potential body weight loss (BWL) was calculated as % $BWL=100-(BW_{days}/BW_{day1} \times 100)$, where day 1 is the first day of treatment and day x is the day of assessment thereafter.

Figure 5:
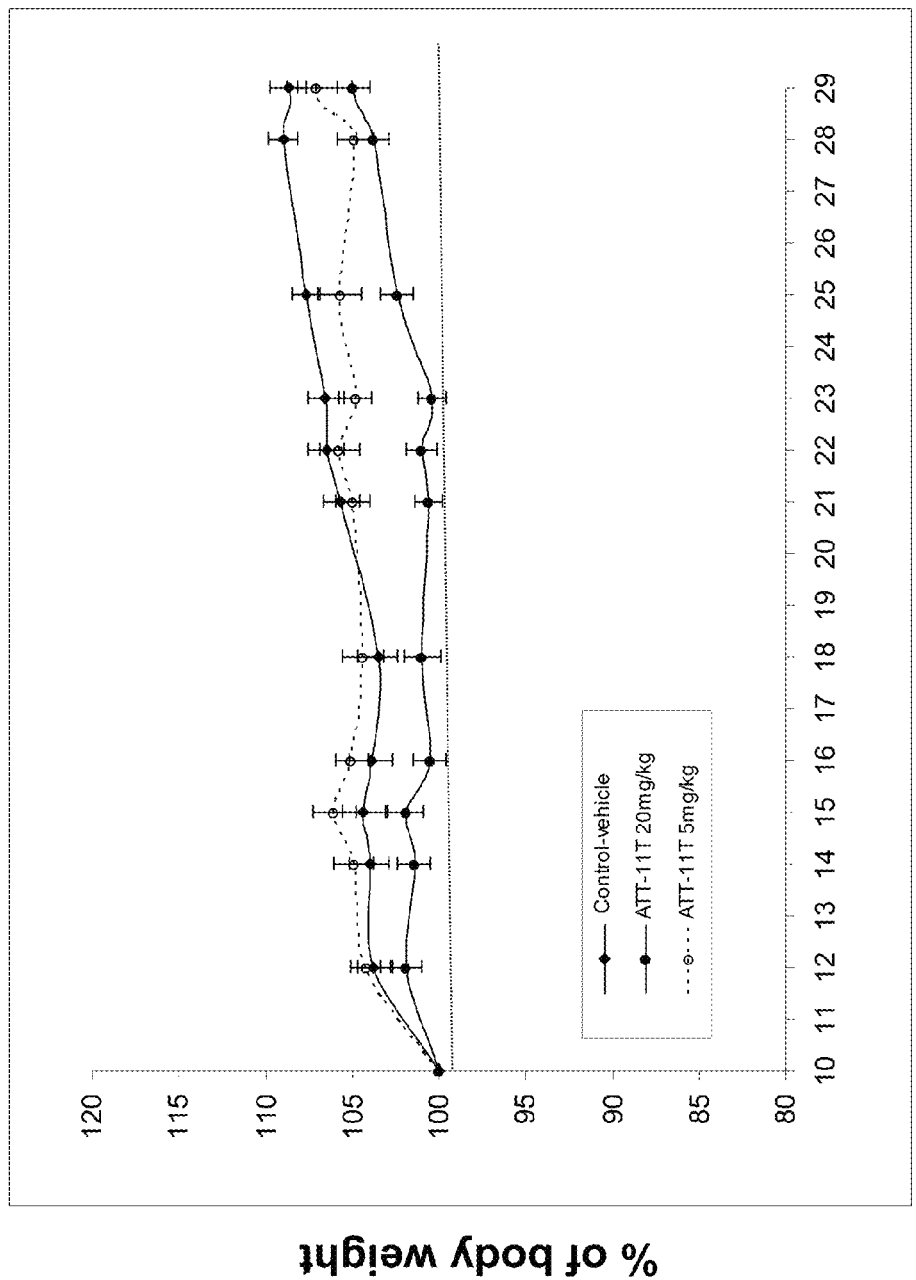
FIG. 5 shows lack of adverse effect of ATT-11T on body weight in the melanoma A375 tumor-bearing mice. Tumor-bearing mice were treated with ATT-11T and were weighed twice a week. As shown, concurrently with the substantial tumor inhibitory effect ATT-11T as described above, the drug was well-tolerated, without causing loss of body weight.

As shown in FIG. 5 in terms of % of initial weight per day starting at day 1 of treatment (day 10 after inoculation) up to day 29 of inoculation, neither loss of body weight nor other adverse effects were observed. The ATT-11T-treated animals gained weight, with the animals treated with 5 mg/kg gaining 7% of initial body weight, and the animals treated with 20 mg/kg gaining 5%.

Therefore, as assessed in these experimental systems, concurrently with its marked effect in induction of tumor regression and in inhibiting tumor growth as described above, ATT-11T was well-tolerated at both doses, without observable adverse effects or weight loss.

Example 6

This example demonstrates pharmacokinetic properties of ATT-11T in dogs

A pharmacokinetics study was performed in beagle dogs, following a single intravenous administration of ATT-11T, while CPT-11 served as comparator. Both drugs were administered to female beagle dogs (Auricoop Ltd, Hungary) at a dose of 6 mg/kg, with subsequent measurement of plasma concentrations over time of both the parent drugs (ATT-11T or CPT-11) and the common active cytotoxic metabolite SN-38.

For this experiment, ATT-11T (Aptuit-Laurus, India), was dissolved in DMSO to prepare a clear stock solution of 50 mg/ml. The stock solution was diluted 10-fold in 10% bovine serum albumin solution in 0.1M sodium phosphate buffer (pH 5.8) and mixed by vortex until a homogeneous emulsion was obtained. CPT-11 (irinotecan hydrochloride trihydrate, Pfizer, USA) was diluted from a concentrate stock solution of 100 mg/5 ml. Fresh formulations of both drugs were prepared prior to each administration, and the drugs were administrated by a slow bolus injection within approximately 3 minutes, at a dose of 6 mg/kg (1.2 ml/kg), adjusted to the individual animal body weight.

For determination of plasma levels of ATT-11T, CPT-11 and SN-38, samples of approximately 3 ml of blood each were collected into EDTA coated vials, containing 75 µl dichlorvos (esterase inhibitor) solution (1.2% (V/V) dichlorvos in saline). Samples were collected once before dosing (0 min) and then at 5 min, 15 min, 30 min, 1 h, 2 h, 4 h, 8 h, 24 h, 48 h, 72 h and 96 h after dosing. Plasma was separated by centrifugation, and stored at −70° C. until HPLC analysis. WinNonlin™ software was used for the analysis of the pharmacokinetic data.

Figure 6A:
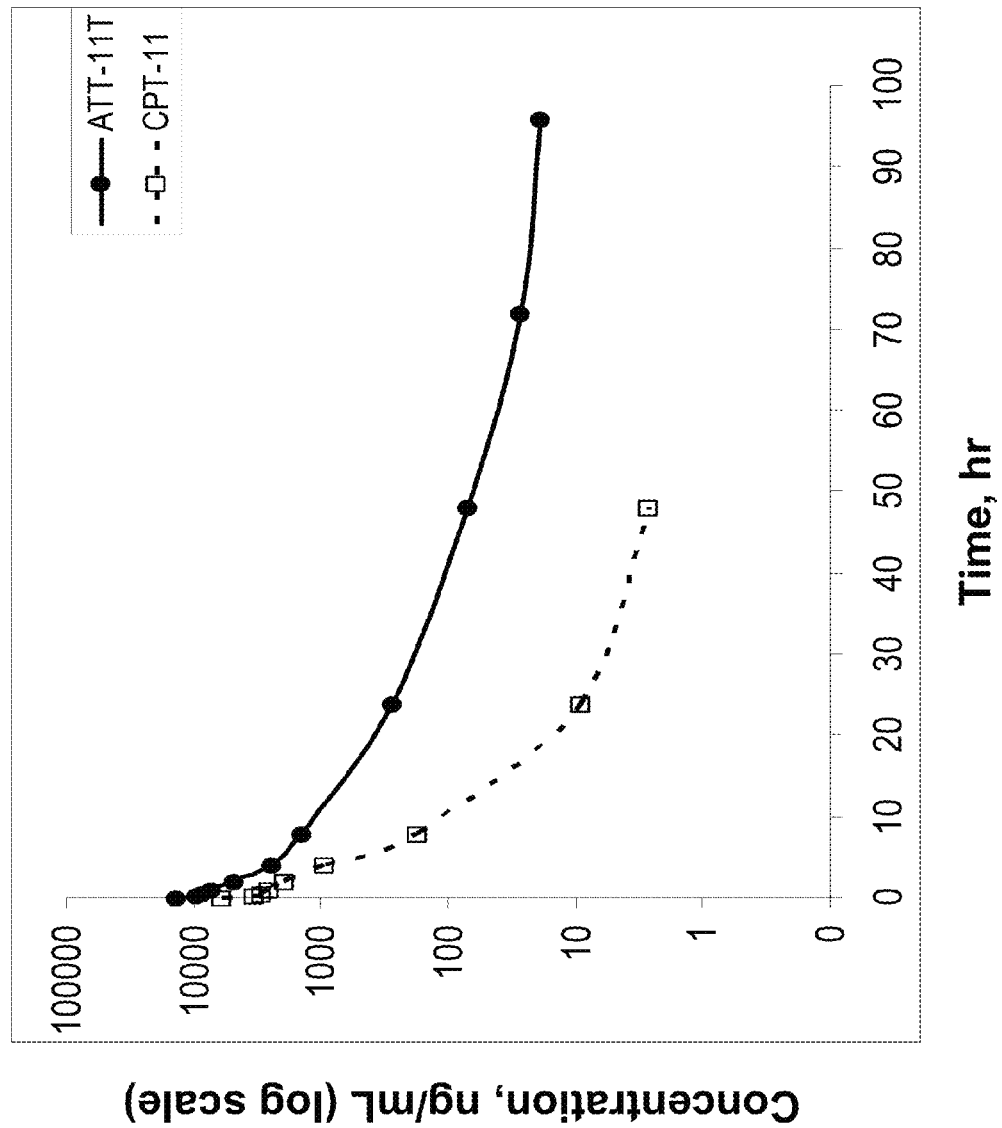
FIGS. 6A and 6B show the pharmacokinetic profile of ATT-11T, as compared to CPT-11 in beagle dogs.
Figure 6B:
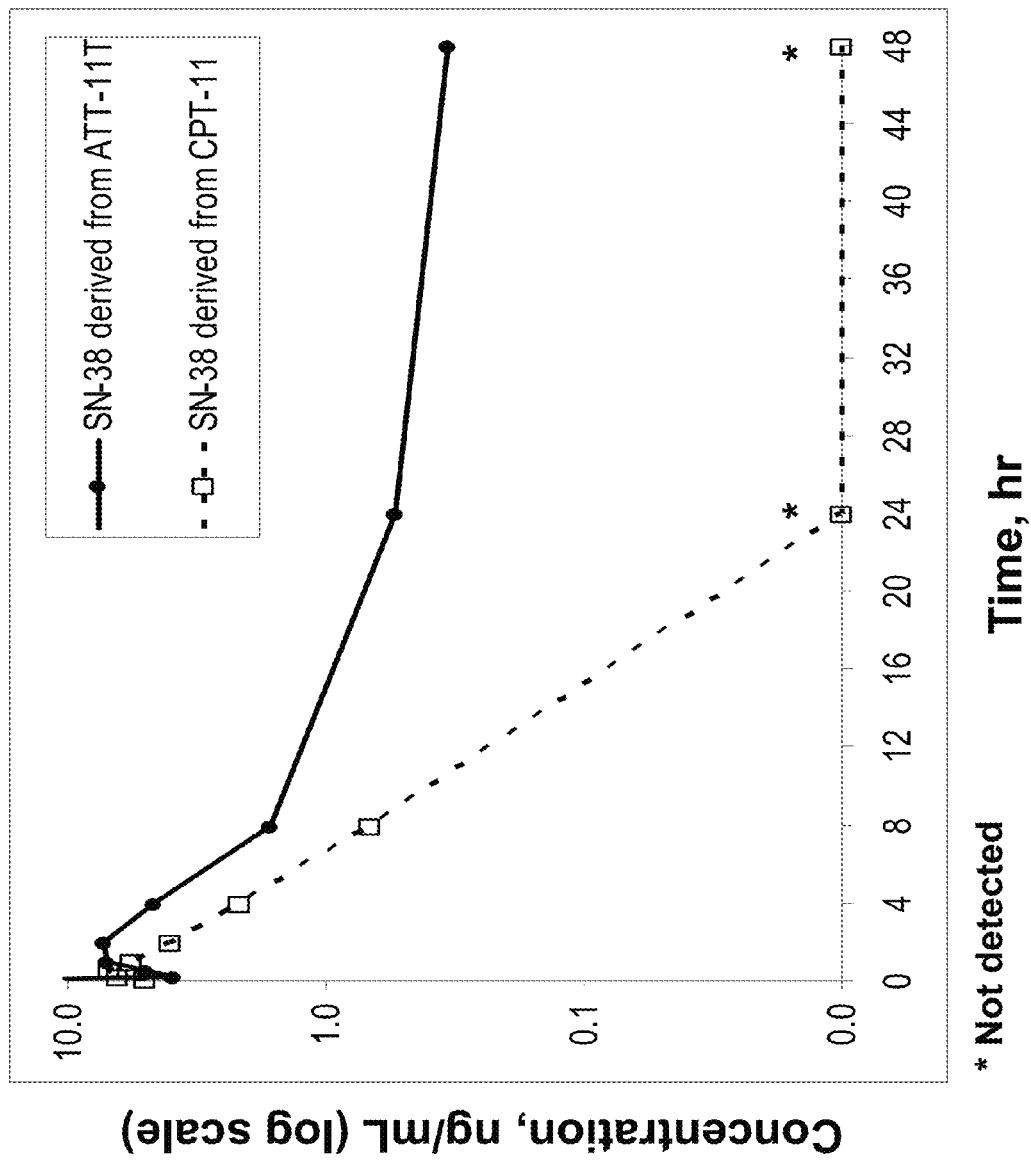

FIG. 6A shows plasma concentrations of the parent drugs ATT-11T or CPT-11 vs. time, while FIG. 6B shows the plasma concentrations of the common active cytotoxic metabolite SN-38 vs. time. As shown, ATT-11T was characterized by sustained plasma levels and slow clearance of both the parent drug and its active metabolite SN-38, as compared to CPT-11. While SN-38 derived from CPT-11 was below detection level already at 24 hours after administration, significant levels of SN-38 derived from ATT-11T were still detectable in the plasma at 48 hours after administration.

Figure 7A:
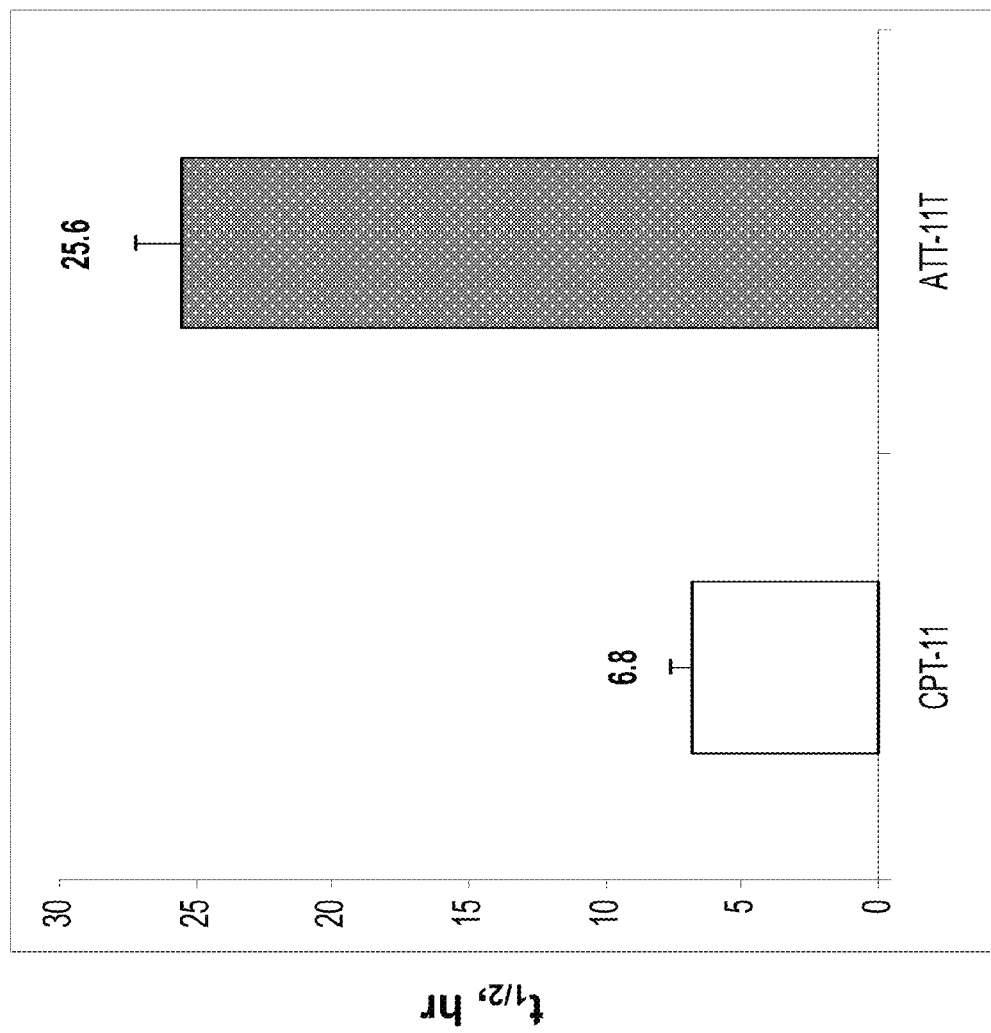
FIGS. 7A and 7B show the plasma half-life ($t_{1/2}$) of the parent drugs (ATT-11T or CPT-11, FIG. 7A), or the active cytotoxic metabolite SN-38, respectively derived from ATT-11T or CPT-11 (FIG. 7B), following intravenous drug administration to dogs. SN-38 derived from ATT-11T manifested a 5.2-fold longer plasma half-life, as compared to SN-38 derived from CPT-11.
Figure 7B:
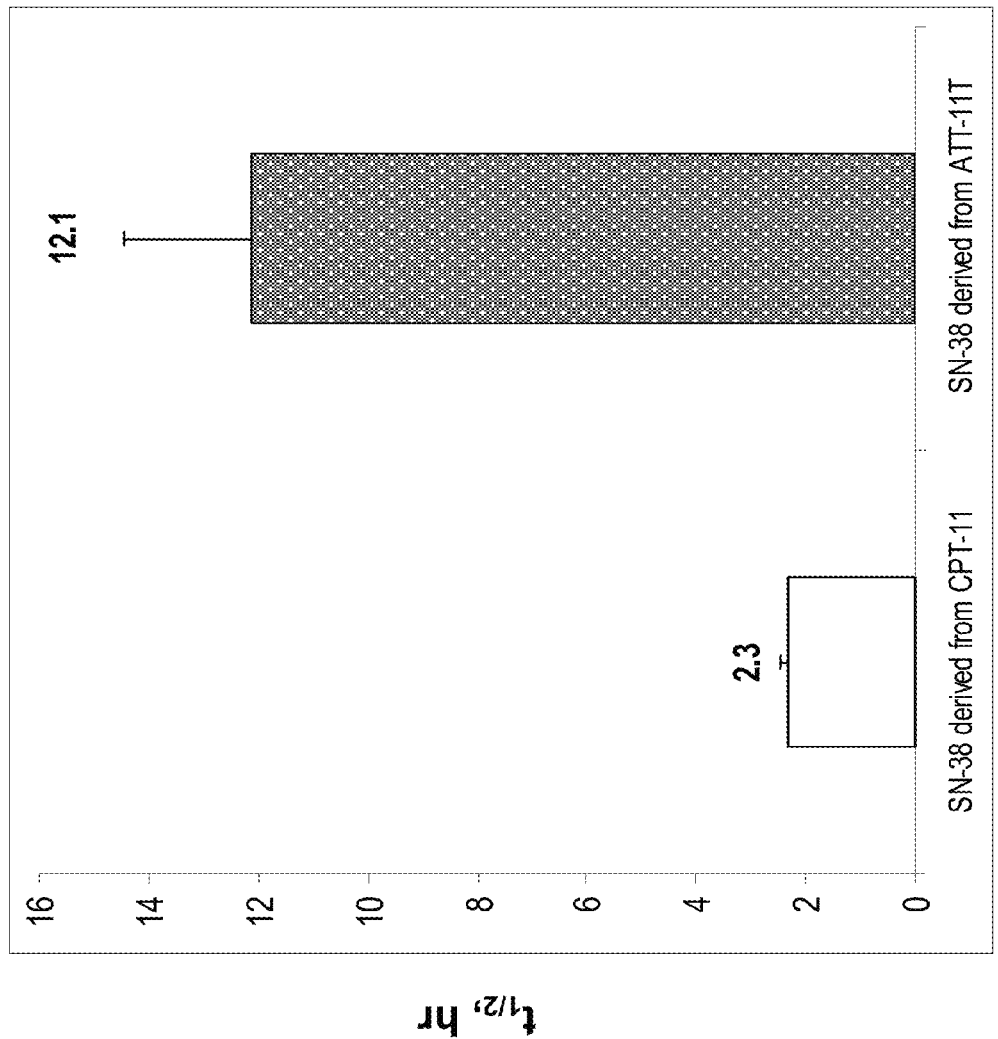

FIGS. 7A and 7B show the plasma half-life ($t_{1/2}$; the time taken to reach a 50% reduction in plasma drug levels) of the parent drug (ATT-11T or CPT-11, FIG. 7A), or the active cytotoxic metabolite SN-38, derived respectively from ATT-11T or CPT-11 (FIG. 7B), following intravenous administration to dogs. ATT-11T showed a $t_{1/2}$ of 25.6 hours compared with 6.8 hours for CPT-11, thus reflecting a 3.8-fold increase in $t_{1/2}$ of ATT11-T over CPT-11 in dogs. Moreover, SN-38 derived from ATT-11T manifested a 5.2-fold longer plasma half-life, as compared to SN-38 derived from CPT-11.

Figure 8A:
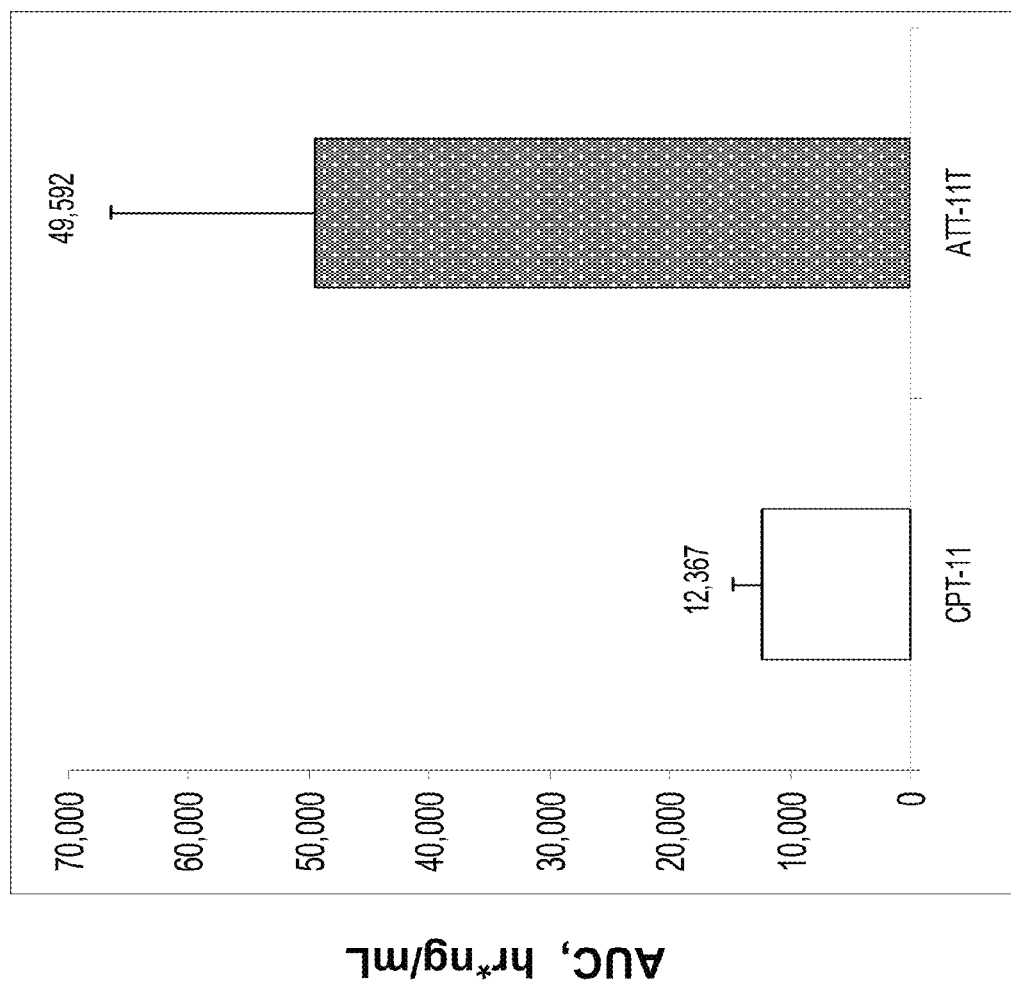
FIGS. 8A and 8B show the area under the plasma concentration/time curve (AUC) of the parent drug (ATT-11T or CPT-11, FIG. 8A), or the common active cytotoxic metabolite SN-38 derived respectively from ATT-11T or CPT-11 (FIG. 8B), following intravenous drug administration to beagle dogs. AUC of ATT-11T was 4-fold larger than that of CPT-11, and the AUC of SN-38 derived from ATT-11T was 2.9-fold larger than the AUC of SN-38 derived from CPT-11.
Figure 8B:
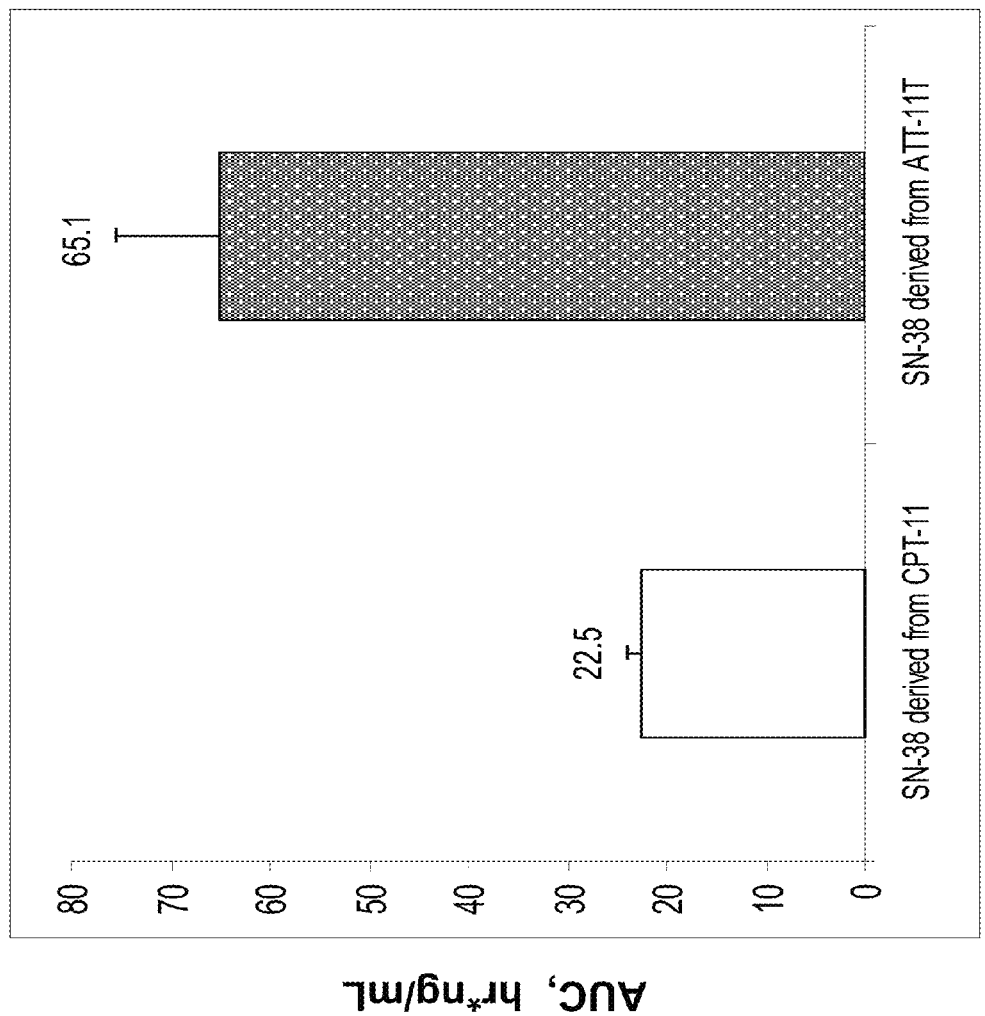

FIGS. 8A and 8B show the area under the plasma concentration/time curve (AUC) of the parents drug (ATT-11T or CPT-11, FIG. 8A), or the active cytotoxic metabolite SN-38 derived respectively from ATT-11T or CPT-11 (FIG. 8B), following intravenous administration to beagle dogs. AUC of ATT-11T was 4-fold larger than that of CPT-11, and the AUC of SN-38 derived from ATT-11T was 2.9-fold larger than the AUC of SN-38 derived from CPT-11.

Taken together, the results of the pharmacokinetic study in the dog demonstrate a favorable profile, with prolonged exposure to both ATT-11T and its active metabolite SN-38, as compared to CPT-11.

Example 7

This example describes several conjugates within the scope of the invention.

Each conjugate comprises the structure as set forth in Formula X, linked, either directly or through a linker (L) according to Formula (I), to a drug (D), used for the treatment of a medical disorder. Said medical disorder may be selected from cancer, inflammatory disorders, immune-mediated disorders, infectious disorders, vascular disorders, toxic disorders, psychiatric disorders or neurological disorders. According to this aspect of the invention, the conjugate or related pharmaceutical composition of the invention may be used for the treatment of the respective medical disorder.

One exemplary conjugate may be used for the treatment of inflammatory disorders. This exemplary conjugate is represented by the structure of Formula V', which includes the structure of Formula X and the anti-inflammatory drug ibuprofen:

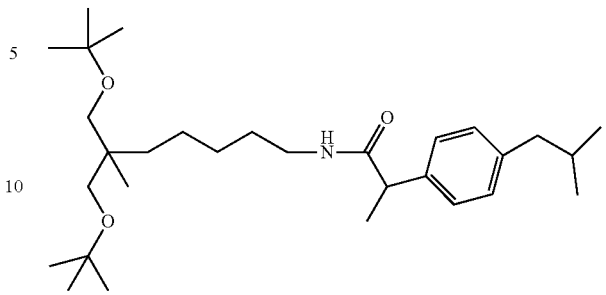

Formula (V')

Another exemplary conjugate may be used for the treatment of Parkinson's disease. This exemplary conjugate is represented by the structure of Formula V''' which includes the structure of Formula (X) and the drug levodopa:

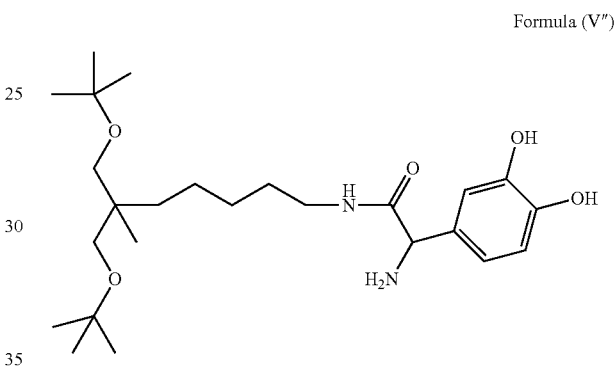

Formula (V'')

These compounds can be evaluated in various pre-clinical models of the respective medical disorders, or in patients having the respective diseases.

Efficacy of the compound according to Formula V' can be evaluated in animal models of inflammation, or in patients having inflammatory diseases such as rheumatoid arthritis, or inflammatory bowel disease.

Efficacy of the compound according to Formula V''' can be evaluated in animal models of Parkinson's disease, such as animals treated with the neurotoxin MPTP or 6-hydroxydopamine. Efficacy of this compound can also be evaluated in patients with Parkinsons' disease, in alleviating the parkinsonian symptoms and signs, such as bradykinesia, rigidity, tremor or postural instability.

Example 8

The efficacy of ATT-11T in inhibiting tumor growth in a xenograft model of small-cell lung carcinoma (11-82) in nude mice in vivo.

Subcutaneous small cell lung carcinoma (SCLC) tumors were established by injection of H-82 SCLC cells ($2.5 \times 10^6$ cells/site) into the right flank of athymic nude mice (female, 8-9 weeks, 8-9 animals/group). Tumor dimensions were measured with a caliper twice a week and tumor volume (mm$^3$) was calculated using the formula: TV=0.52 L×W$^2$, where L and W are the major and minor dimensions of the tumor, respectively. Drug treatment was initiated on day 15, when tumors reached an average volume of 162 mm$^3$ ATT-11T was administered intravenously into the tail vein of the mice, in a vehicle comprising 6.5% Cremophor, 3.5% ETOH and 90% of 0.4% DOC solution. The drug was administered at a dose of 40 mg/kg, given once a week for three weeks. In the accompanying figure a triangular mark on the X axis indicates days on which the drug was administered. Irinotecan hydrochloride on the basis of the trihydrate salt (CPT-11, Teva Pharmaceuticals) was purchased as a 20 mg/ml stock solution and was administered intravenously as well, diluted in saline, at a dose of 36 mg/kg to a second group of mice. The equimolar doses of CPT-1 1were 10% less than ATT-11T due to the higher molecular weight of ATT-11T. CPT-11 was also administered once a week for three weeks. Tumor-bearing mice, which served as the control group, did not receive any treatment.

FIG. 9 shows the tumor volumes (mm$^3$) vs. days after tumor inoculation. As shown, ATT-11T provided an inhibitory effect on tumor growth. While tumors of the control group, i.e., untreated animals, showed rapid growth. ATT-11T caused 92% tumor growth inhibition vs. the control group, compared to 67% inhibition achieved by CPT-11 treatment. As shown, ATT-11T treatment resulted in substantial growth inhibition compared with CPT-11, thus demonstrating the potent anti-cancer activity of ATT-11T when treating SCLC in vivo.

Example 9

The Efficacy of ATT-11T in Inhibiting Tumor Growth in a Xenograft Model of Pancreatic Carcinoma in Nude Mice In Vivo Subcutaneous pancreatic carcinoma tumors were established by injection of Mia-PaCa cells (2×10$^6$ cells/site) into the right flank region of athymic nude mice (female, 8-9 weeks, 8-9 animals/group). Tumor volume (mm$^3$) was calculated as describe above (for example as describe with reference to Example 8). Drug treatment was initiated on day 13, when tumors reached an average volume of 164 mm$^3$. A dose of 40 mg/kg of ATT-11T was administered intravenously into the tail vein of a first group of mice, in a vehicle comprising 6.5% Cremophor, 3.5% ETOH and 90% of 0.4% DOC solution. Irinotecan hydrochloride on the basis of the trihydrate salt (CPT-11) was purchased as a 20 mg/ml stock solution and was diluted in saline to reach a concentration of 3.6 mg/ml for the dose of 36 mg/kg and was administered to a second group of mice. The equimolar doses of CPT-1 1were 10% less than ATT-11T due to the higher molecular weight of ATT-11T.

The drugs were administered once a week for three weeks. In the accompanying figure a triangular mark on the X axis indicates days on which the drug was administered. The group of tumor bearing mice which served as the control did not receive any treatment.

FIG. 10A shows the tumor volume (mm$^3$) vs. days after tumor inoculation. As shown, ATT-11T presented a dramatic inhibitory effect on tumor growth. While tumors of the control group, i.e., untreated animals, presented rapid growth, ATT-11T caused 86% growth inhibition vs. control tumors compared to 42% growth inhibition achieved by CPT-11, one week after the last administration of the drug.

The Efficacy of ATT-11T in Inhibiting Tumor Growth in a Xenograft Model of Pancreatic Carcinoma in Nude Mice In Vivo: Dose Response Subcutaneous pancreatic carcinoma tumors were established and their dimensions were measured as described above. Drug treatment was initiated on day 13, when tumors reached an average volume of 164 mm$^3$. A stock solution of ATT-11T was prepared by dissolving ATT-11T powder in 65% Cremophor-EL, 35% ETOH solution to yield a concentration of 40 and 20 mg/ml. These stock solutions were further diluted right before injection in 0.4% DOC to reach a solution of 4 and 2 mg/ml for doses of 40 mg/kg and 20 mg/kg, respectively. The drug was administered once a week for three weeks. In the accompanying figure a triangular marks on the X axis indicate days on which the drug was administered. The group of tumor bearing mice which served as the control did not receive any treatment.

FIG. 10B shows the tumor volume (mm3) vs. days after tumor inoculation. As shown, intravenous administration of ATT-11T demonstrated dose response dependent efficacy in Mia-PaCa2 model. Treatment with ATT-11T once a week for 3 weeks, in doses of 40 mg/kg and 20 mg/kg resulted in tumor growth inhibition (TGI) of 86% and 48%, respectively, one week after the last administration of the drug.

Effect of Treatment of Pancreatic Cancer with ATT-11T Administered i.v.Vs. Equimolar Doses of CPT-11 on % Tumor Growth Delay The secondary treatment efficacy endpoint was evaluated by calculating the percentage of tumor growth delay (% TGD). Tumor growth delay is defined as the difference in days for treated versus control tumors to reach a specified volume, 1,000 mm$^3$. Tumor growth delay was evaluated from the data of all animals, excluding only animals that died due to treatment-related, non-treatment-related adverse events, and those that developed extensive tumor necrosis or when individual tumor size deviated±2SE from the mean tumor volume of the group on or before the day of TGD analysis. Percent tumor growth delay (% TGD) was defined as the difference between the mean time (days) it took a drug treated group to reach a tumor volume of 1,000 mm$^3$ and the mean time (days) it took the control group to reach the same tumor volume, expressed as a percentage of the mean time of the control group:

% $TGD = [(T_{drug-treated} - T_{control})/T_{control}] \times 100$ where:

$T_{drug-treated}$=mean time (days) for the drug treated group to reach a tumor volume of 1,000 mm3

$T_{control}$=mean time (days) for the control group to reach a tumor volume of 1,000 mm$^3$ Pancreatic carcinoma tumors treated with ATT-11T at a dose of 40 mg/kg i.v. once a week for 3 weeks, reached an average tumor volume of 1,000 mm$^3$ 53 days post tumor inoculation, i.e. resulted in % TGD of 152%. This value is twice as high as that of the group which was treated with CPT-11 at equimolar dose of 36 mg/kg i.v. and achieved a TGD of 76%.

Pancreatic carcinoma tumors treated with ATT-11T at a dose of 20 mg/kg i.v. once a week for 3 weeks, reached an average tumor volume of 1,000 mm$^3$ 39 days post tumor inoculation, i.e. resulted in % TGD of 86%. This value is twice as high as that of the group which was treated with CPT-11 at equimolar dose of 18 mg/kg i.v. and achieved a TGD of 43%.

Example 10

The Efficacy of ATT-11T in Inducing Tumor Regression and in Inhibiting and Delaying Tumor Growth in a Xenograft Model of Colorectal Carcinoma in Nude Mice In Vivo Subcutaneous colorectal carcinoma tumors were established by injection of SW-620 colorectal carcinoma cells (2×10$^6$ cells/site) into the right flank region of athymic nude mice (female, 8-9 weeks, 8-9 animals/group). Tumor volumes (mm³) were calculated as described above (for example as describe with reference to Example 8). Drug treatment was initiated on day 11, when tumors reached an average volume of 119 mm³ ATT-11T was administered in a vehicle comprising 5% DMSO, 5% NMP, 10% ETOH, 40% PEG-400 and 40% PG. CPT-11 was administered as hydrochloride trihydrate, diluted in saline from a concentrate stock solution of 20 mg/ml. ATT-11T was administered at a dose of 150 mg/kg (the maximal tolerate dose (MTD) of ATT-11T) to a first group of mice and CPT-11 was administered to a second group of mice at a dose of 100 mg/kg (the MTD of CPT-11), once a week for three weeks. In the accompanying figure a triangular marks on the X axis indicate days on which the drug was administered. The drugs were administered intraperitoneally. The control group did not receive any treatment. The ATT-11T vehicle showed no effect on tumor growth or on body weight loss. ATT-11T treated group at MTD (150 mg/kg) resulted in 100% tumor growth inhibition compared to only 85% achieved by CPT-11 treated group with MTD (100 mg/kg).

FIG. 11A shows the tumor volume (mm³) vs. days after tumor inoculation. As demonstrated, ATT-11T treated group with MTD (150 mg/kg) presented a dramatic inhibitory effect on tumor growth. While tumors of the control untreated animals manifested rapid growth.

ATT-11T treatment led to complete tumor regression and 100% growth inhibition, one week after the last administration of the drug compared with CPT-11 treated group with MTD (100 mg/kg) which achieved 85% inhibition in comparison to the control group.

As shown in FIG. 11B, assessment of the tumor growth rate 136 days following the last dose of treatment (161 days after tumor cell inoculation) revealed rapid tumor growth in the CPT-11-treated group, starting soon after the administration of the last dose of the drug. Accordingly, the control group and the MTD (100 mg/kg) of CPT-11 treated group reached the end point tumor volume of 1000 mm³ on days 32 and 70 post tumor inoculation, respectively. In contrast, the animals treated with the MTD (150 mg/kg) of ATT-11T showed no tumor growth even 136 days post last treatment and 161 days post tumor inoculation.

Taken together, these results indicate that ATT-11T has potent anti-tumor properties when treating colorectal carcinoma, being able to induce both tumor regression and prolonged tumor growth inhibition in the SW-620 model.

Example 11

The Efficacy of ATT-11T in Inducing Tumor Regression and in Inhibiting and Delaying Tumor Growth in a Xenograft Model of Ovarian Carcinoma in Nude Mice In Vivo Ovarian carcinoma tumors, OVCAR-3 were established by subcutaneous transplantation of tumor fragments in a volume of approximately 1 mm³ each, into the right flank region of athymic nude mice (female, 8-9 weeks, 10 animals/group). Drug treatment was initiated on day 1, when tumors reached an average volume of 80-120 mm³ ATT-11T was administered intravenously into the tail vein of a first group of mice, in a vehicle comprising 10% DMSO and 10% bovine serum albumin (BSA) in 0.1M sodium phosphate buffer (pH 5.8). CPT-11 was diluted in saline and administered to a second group of mice. The drugs were administered i.v. at a dose of 20 mg/kg and 18 mg/kg for ATT-11T and CPT-11, respectively, once a week for three weeks. In the accompanying figure a triangular marks on the X axis indicate days on which the drug was administered. Tumor-bearing mice, injected only with the vehicle solution served as the control group.

FIG. 12A shows the tumor volume (mm³) vs. days after tumor inoculation. As shown, ATT-11T presented a dramatic inhibitory effect on tumor growth. While tumors of the control group, i.e., untreated animals, presented rapid tumor growth, ATT-11T caused complete tumor regression and 99% growth inhibition vs. the control group compared to CPT-11, which achieved inhibition of 83% compared to the control group, one week post last administration of the drug. As shown, ATT-11T caused complete tumor regression and tumor growth inhibition compared with CPT-11, thus demonstrating its potent anti-cancer activity in vivo, when treating ovarian carcinoma.

Assessment of the tumor growth rate 21 days following the last dose of treatment revealed rapid tumor growth in the CPT-11-treated group, starting soon after the administration of the last dose of the drug. Further, the control group reached an average tumor volume of 932 mm³ already on day 25 and the equimolar CPT-11 treated group reached an average tumor volume of 819 mm³ on day 39 (18 days post last dose). In contrast, the ATT-11T treated group, which showed limited tumor recovery reached an average tumor volume of 46 mm³ on day 42 (21 days post last dose), as presented in FIG. 12B.

Taken together, these results indicate that ATT-11T has potent anti-tumor properties, being able to induce both tumor regression and prolonged inhibition of tumor growth when treating ovarian carcinoma.

The invention claimed is:

1. A method of treating pancreatic cancer in a subject in need comprising administering to the subject a therapeutically effective dose of compound represented by the structure set forth in Formula (II)

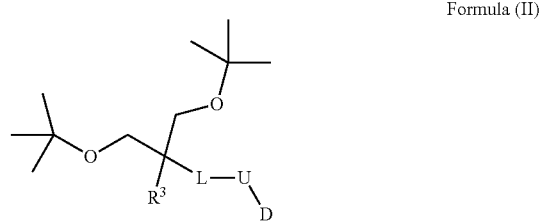

Formula (II)

in which

R³ is selected from the group consisting of hydrogen, $C_1$, $C_2$, $C_3$, $C_4$, $C_5$, $C_6$, $C_7$ and $C_8$ linear or branched alkyl;

L is selected from the group consisting of $C_1$, $C_2$, $C_3$, $C_4$, $C_5$, $C_6$, $C_7$ or $C_8$ linear, branched or cyclic alkyl, $C_1$, $C_2$, $C_3$, $C_4$, $C_5$, $C_6$, $C_7$ or $C_8$ linear, branched alkyl-amine, piperidinyl, aryl, and a combination thereof;

U is selected from the group consisting of —O—; —(CO) O—; —O(CO)—NH—; and —(CO)—NH—;

D is an anti-cancer drug; and pharmaceutically acceptable salts, hydrates, solvates and metal chelates of the compound.

2. The method according to claim 1 wherein R³ is a methyl.

3. The method according to claim 2 comprising administering to the subject in need a compound according to the structure set forth in Formula (III)

Formula (III)

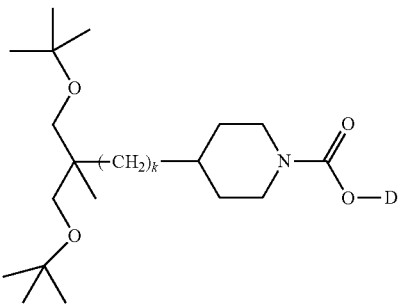

wherein k is an integer selected from the group consisting of 1, 2, 3, 4 and 5;
and pharmaceutically acceptable salts, hydrates, solvates and metal chelates of the compound.

4. The method according to claim 2 comprising administering to the subject in need a compound according to the structure set forth in Formula (IV)

Formula (IV)

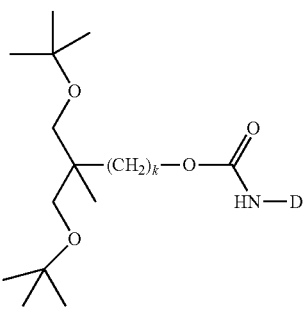

wherein k is an integer selected from the group consisting of 1, 2 or 3;
and pharmaceutically acceptable salts, hydrates, solvates and metal chelates of the compound.

5. The method according to claim 2 comprising administering to the subject in need a compound according to the structure set forth in Formula (VI)

Formula (VI)

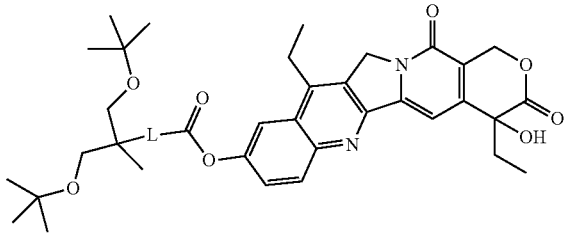

and pharmaceutically acceptable salts, hydrates, solvates and metal chelates of the compound.

6. The method according to claim 5 comprising administering to the subject in need a compound according to the structure set forth in Formula (VII)

Formula (VII)

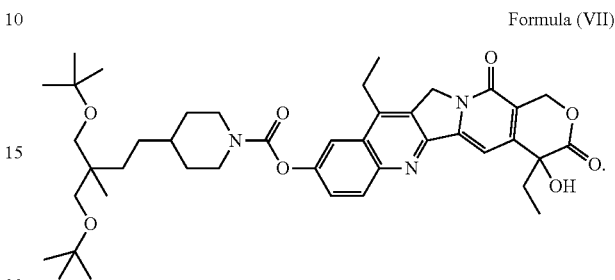

7. The method according to claim 4 comprising administering to the subject in need a compound according to the structure set forth in Formula (VIII)

Formula (VIII)

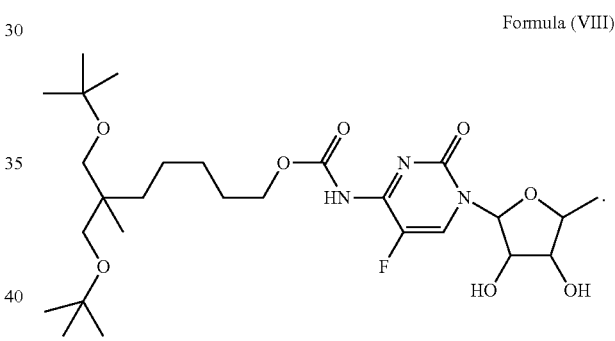

8. The method according to claim 1 wherein D is a topoisomerase inhibitor.

9. The method according to claim 8 wherein D is a camptothecin.

10. The method according to claim 8 wherein D is 5-fluorouracil.

11. The method according to claim 10 wherein D is capecitabine.

* * * * *